US012622961B2

(12) United States Patent
Meredith et al.

(10) Patent No.: US 12,622,961 B2
(45) Date of Patent: May 12, 2026

(54) LIPOPOLYSACCHARIDE MOLECULES FOR ENHANCING IMMUNE RESPONSES

(71) Applicant: The Penn State Research Foundation, University Park, PA (US)

(72) Inventors: Timothy Meredith, University Park, PA (US); Gloria Komazin, University Park, PA (US); Michael A. Maybin, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 1082 days.

(21) Appl. No.: 17/641,760

(22) PCT Filed: Sep. 10, 2020

(86) PCT No.: PCT/US2020/050260
§ 371 (c)(1),
(2) Date: Mar. 9, 2022

(87) PCT Pub. No.: WO2021/050778
PCT Pub. Date: Mar. 18, 2021

(65) Prior Publication Data
US 2022/0339283 A1      Oct. 27, 2022

Related U.S. Application Data

(60) Provisional application No. 62/898,458, filed on Sep. 10, 2019.

(51) Int. Cl.
A61K 39/39 (2006.01)
C07H 13/06 (2006.01)
A61K 39/00 (2006.01)

(52) U.S. Cl.
CPC ............. *A61K 39/39* (2013.01); *C07H 13/06* (2013.01); *A61K 2039/55572* (2013.01)

(58) Field of Classification Search
None
See application file for complete search history.

(56) References Cited

U.S. PATENT DOCUMENTS

| | | | |
|---|---|---|---|
| 7,491,707 | B1 | 2/2009 | Jiang et al. |
| 2009/0035294 | A1 | 2/2009 | Mahe et al. |
| 2010/0168054 | A1 | 7/2010 | Moutel et al. |
| 2015/0110854 | A1 | 4/2015 | Shaw et al. |
| 2017/0368161 | A1 | 12/2017 | Jones et al. |

*Primary Examiner* — Karl J Puttlitz
(74) *Attorney, Agent, or Firm* — Hodgson Russ LLP

(57) ABSTRACT

The present disclosure provides compositions and methods for enhancing immune response in a subject. In an embodiment, this disclosure provides modified LPS molecules and compositions comprising the modified LPS molecules. The disclosure also provides methods for enhancing an immune response in a subject.

14 Claims, 24 Drawing Sheets
Specification includes a Sequence Listing.

A.

—/— Phosphoethanolamine ● Glucose ● *L-glycero-D-manno-heptose*
— Phosphate ● 3-deoxy-α-D-*manno*-oct-2-ulosonate ● D-glucosamine

A.

| ArnA | + | - | + | - | - | - |
| EptA | + | + | - | - | - | - (P) |
| LpcA | + | + | + | + | - | - |

B.

| EptA | - | - | - | - | - | - | - (P) | - (P) |
| EptB | + | - | + | + | - | + (P) | + | + |
| EptC | + | + | - | + | + (P) | - | - | + |
| WaaP | + | + | + | - | + | + | + | - |

C.

A.

| Strain | Saccharide Core | EptA | Acylation State |
|---|---|---|---|
| GKM374 | complete | no | hexa |
| TXM402 | complete | yes | hexa |
| TXM418 | complete | no | penta |
| TXM419 | complete | yes | penta |
| GKM499 | complete | no | tetra |
| GKM502 | complete | yes | tetra |
| GKM445 | truncated | no | tetra |
| GKM446 | truncated | yes | tetra |

A.

B.

Green

SEQUENCE LISTING

<160> NUMBER OF SEQ ID NOS: 42

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
ggtgacctgc cttaccacaa c                                                      21

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tcgtgatgtt tagccgcttc                                                        20

<210> SEQ ID NO 3
<211> LENGTH: 60
<212> TYPE: DNA
<213> ORGANISM: Artificial Sequence
<220> FEATURE:
<223> OTHER INFORMATION: Primer

<400> SEQUENCE: 3
gttggccgct ttttatatct ctatctgcct gaatattgcc ttgcgcctac ctgtgacgga          60

<210> SEQ ID NO 4
<211> LENGTH: 60
<212> TYPE: DNA
<213> ORGANISM: Artificial Sequence
<220> FEATURE:
<223> OTHER INFORMATION: Primer

<400> SEQUENCE: 4
tgttgcgttt gcgcctgttt ttgcaggcag ttctggtcaa cccttacgcc ccgccctgcc          60

<210> SEQ ID NO 5
<211> LENGTH: 60
<212> TYPE: DNA
<213> ORGANISM: Artificial Sequence
<220> FEATURE:
<223> OTHER INFORMATION: Primer

<400> SEQUENCE: 5
cactgcattt tgtctattac atttatgctg aaggatatcc tcctcgaatt gacataagcc          60

<210> SEQ ID NO 6
<211> LENGTH: 60
<212> TYPE: DNA
<213> ORGANISM: Artificial Sequence
<220> FEATURE:
<223> OTHER INFORMATION: Primer

<400> SEQUENCE: 6
tgccggatgc ggcgtaaacg tcttatccgg cctacgccag acgtcggctt gaacgaattg          60

<210> SEQ ID NO 7
<211> LENGTH: 60
<212> TYPE: DNA
<213> ORGANISM: Artificial Sequence

```
<220> FEATURE:
<223> OTHER INFORMATION: Primer

<400> SEQUENCE: 7
agccgtttgc cacgttatgg cgcggtaaag atccttttga ggctcgaatt gacataagcc        60

<210> SEQ ID NO 8
<211> LENGTH: 60
<212> TYPE: DNA
<213> ORGANISM: Artificial Sequence
<220> FEATURE:
<223> OTHER INFORMATION: Primer

<400> SEQUENCE: 8
cgttctttcc ctgatttttg tggctttttgc ttctgcttgc gagtcggctt gaacgaattg        60

<210> SEQ ID NO 9
<211> LENGTH: 60
<212> TYPE: DNA
<213> ORGANISM: Artificial Sequence
<220> FEATURE:
<223> OTHER INFORMATION: Primer

<400> SEQUENCE: 9
gatacatcaa atcgattaca cagcagaagc tgagcttttt gcctcgaatt gacataagcc        60

<210> SEQ ID NO 10
<211> LENGTH: 60
<212> TYPE: DNA
<213> ORGANISM: Artificial Sequence
<220> FEATURE:
<223> OTHER INFORMATION: Primer

<400> SEQUENCE: 10
gttagccgct gcctcttttg cctgcgggat gtgacaccag tttacggctt gaacgaattg        60

<210> SEQ ID NO 11
<211> LENGTH: 60
<212> TYPE: DNA
<213> ORGANISM: Artificial Sequence
<220> FEATURE:
<223> OTHER INFORMATION: Primer

<400> SEQUENCE: 11
gcattccaca gaagtccagg ctaaacctct ttttagctgg aactcgaatt gacataagcc        60

<210> SEQ ID NO 12
<211> LENGTH: 60
<212> TYPE: DNA
<213> ORGANISM: Artificial Sequence
<220> FEATURE:
<223> OTHER INFORMATION: Primer

<400> SEQUENCE: 12
ctgattaccc acctgatcgc catacggcag tgtgtcgtaa tctacggctt gaacgaattg        60

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
gatttttgcc ttatccgaaa ctgg                                               24
```

-continued

```
<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
caggcgaagg cctctcctcg cgag                                       24

<210> SEQ ID NO 15
<211> LENGTH: 60
<212> TYPE: DNA
<213> ORGANISM: Artificial Sequence
<220> FEATURE:
<223> OTHER INFORMATION: Primer

<400> SEQUENCE: 15
ctacccaagt tctccaccgc actgcttcat ccgcgttatt ggtcacctag atccttttgg    60

<210> SEQ ID NO 16
<211> LENGTH: 60
<212> TYPE: DNA
<213> ORGANISM: Artificial Sequence
<220> FEATURE:
<223> OTHER INFORMATION: Primer

<400> SEQUENCE: 16
tccgggcgtg ttttaaagcg acggtgtaac cacatatact gccgttctcc gctcatgagc    60

<210> SEQ ID NO 17
<211> LENGTH: 60
<212> TYPE: DNA
<213> ORGANISM: Artificial Sequence
<220> FEATURE:
<223> OTHER INFORMATION: Primer

<400> SEQUENCE: 17
gttttatggt cacaaatgaa cgtgagtaaa tatgtcgcta tcctatgacc atgattacgc    60

<210> SEQ ID NO 18
<211> LENGTH: 60
<212> TYPE: DNA
<213> ORGANISM: Artificial Sequence
<220> FEATURE:
<223> OTHER INFORMATION: Primer

<400> SEQUENCE: 18
actaaaactt catttgtctc aaaactgaaa gcgcatccag gcacgttgta aaacgacggc    60

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
cgagcgtgag tttggtgaat cc                                         22

<210> SEQ ID NO 20
<211> LENGTH: 20
<212> TYPE: DNA
<213> ORGANISM: Artificial Sequence
<220> FEATURE:
<223> OTHER INFORMATION: Primer
```

-continued

```
<400> SEQUENCE: 20
ccgatcccag ttaccgctac                                           20

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
aaacccgtat cccttagatg cacc                                      24

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
ctcaaggctt tgttccgcca tc                                        22

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
aggtctgacc acttgtgatg                                           20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
attattcggc ctacggttcg                                           20

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
gataagcaaa tcgccgattt ccag                                      24

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
tgtcttattg atcatctctt gtgg                                      24

<210> SEQ ID NO 27
```

```
<211> LENGTH: 24
<212> TYPE: DNA
<213> ORGANISM: Artificial Sequence
<220> FEATURE:
<223> OTHER INFORMATION: Primer

<400> SEQUENCE: 27
cagggtgtta tcacctgttt gtcc                                               24

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
ccttttgatc ggcgagaaag tcagc                                             25

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
ccttaaggaa ttgtcgttac attcg                                             25

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
gcatccggca aatagcgcct ggctg                                             25

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31
ctggcgcagg ccaaagagat tgtgc                                             25

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
gtagagtaag tacgttgccg gatgc                                             25

<210> SEQ ID NO 33
<211> LENGTH: 28
<212> TYPE: DNA
<213> ORGANISM: Artificial Sequence
<220> FEATURE:
<223> OTHER INFORMATION: Primer

<400> SEQUENCE: 33
```
ggttgcgggc gaaaaaatgc gacaatac                                          28

<210> SEQ ID NO 34
<211> LENGTH: 27
<212> TYPE: DNA
<213> ORGANISM: Artificial Sequence
<220> FEATURE:
<223> OTHER INFORMATION: Primer

<400> SEQUENCE: 34
gggagattta atagcgtgaa ggaacgc                                           27

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
gtagctttgc tatgctagta gtag                                             24

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
gtggtacgct ttgtccagtg taac                                             24

<210> SEQ ID NO 37
<211> LENGTH: 32
<212> TYPE: DNA
<213> ORGANISM: Artificial Sequence
<220> FEATURE:
<223> OTHER INFORMATION: Primer

<400> SEQUENCE: 37
gcggccgcgc gaattaattt tgctttgcga gc                                    32

<210> SEQ ID NO 38
<211> LENGTH: 31
<212> TYPE: DNA
<213> ORGANISM: Artificial Sequence
<220> FEATURE:
<223> OTHER INFORMATION: Primer

<400> SEQUENCE: 38
cgactctaga ggatccgtct tcaacaatca g                                     31

<210> SEQ ID NO 39
<211> LENGTH: 32
<212> TYPE: DNA
<213> ORGANISM: Artificial Sequence
<220> FEATURE:
<223> OTHER INFORMATION: Primer

<400> SEQUENCE: 39
gcggccgcgc gaattctaag cagggtgtta tc                                    32

<210> SEQ ID NO 40
<211> LENGTH: 33
<212> TYPE: DNA

-continued

```
<213> ORGANISM: Artificial Sequence
<220> FEATURE:
<223> OTHER INFORMATION: Primer

<400> SEQUENCE: 40
cgactctaga ggatccggcg agaaagtcag cag                                33

<210> SEQ ID NO 41
<211> LENGTH: 33
<212> TYPE: DNA
<213> ORGANISM: Artificial Sequence
<220> FEATURE:
<223> OTHER INFORMATION: Primer

<400> SEQUENCE: 41
gcggccgcgc gaattctgtc gttacattcg gcg                                33

<210> SEQ ID NO 42
<211> LENGTH: 34
<212> TYPE: DNA
<213> ORGANISM: Artificial Sequence
<220> FEATURE:
<223> OTHER INFORMATION: Primer

<400> SEQUENCE: 42
cgactctaga ggatccgcaa atagcgcctg gctg                               34
```

LIPOPOLYSACCHARIDE MOLECULES FOR ENHANCING IMMUNE RESPONSES

CROSS REFERENCE TO RELATED APPLICATIONS

This application claims priority to U.S. Provisional Application No. 62/898,458, filed Sep. 10, 2019, the disclosure of which is incorporated herein by reference.

STATEMENT REGARDING FEDERALLY SPONSORED RESEARCH AND DEVELOPMENT

This invention was made with government support under grant no. R21 AI138152 awarded by the National Institutes of Health. The government has certain rights in the invention.

BACKGROUND OF THE DISCLOSURE

Vaccines are biological compositions that elicit an immune response against a particular diseased condition. Vaccines may be preventative (preventing or attenuating the effects of a future infection), or therapeutic (administered after onset of a condition, such as, cancer). Most vaccines are designed empirically using inactivated or attenuated pathogens. While adjuvants are commonly used to improve vaccine efficacy, associated side-effects of promising adjuvants have hindered their wide-spread use. For example, LPS, a glycolipid consisting of a lipid A anchor within the bilayer, and a set of covalently attached core saccharides, is a potent activator of immune responses. However, LPS is toxic to humans and animals due to hyper-activation of inflammatory immune responses. While modified forms of LPS (such as acetylated forms) with reduced toxicity have been reported, the less toxic variants generally also have reduced immunostimulatory properties. For example, it is known that while under-acylated forms of LPS such as lipid $IV_A$ are less toxic, they also have lower Toll-like receptor 4 (TLR4) receptor activity, lead to less cytokine production, and weaker adjuvancy. As such, there is a continuing need for development of adjuvants that enhance immune responses while being well-tolerated.

SUMMARY OF THE DISCLOSURE

This disclosure provides compositions and methods for enhancing immune response in a subject. In an embodiment, this disclosure provides modified LPS molecules and compositions comprising the modified LPS molecules. The disclosure also provides methods for enhancing an immune response in a subject.

The human immune system can detect picogram levels of LPS through Toll-like receptor 4 signaling, which leads to induction of a proinflammatory response and secretion of cytokines and other second messengers. The cytokine/chemokine response to LPS and other TLR4 agonists in part orchestrates the production of antibodies to provide long-term humoral immunity. Co-administration of LPS and analogs with targeted antigens (from cancer cells, viruses, etc) in vaccine formulations can thus boost antibody production through adjuvancy. LPS (hexa-acylation state, with or without modifications) is generally too potent to be of use in vaccines; however, as the robust TLR4 response induces fever, vasodilation, and general toxicity.

This disclosure provides modified lipopolysaccharide (LPS) molecules that act as vaccine adjuvants to enhance immune responses to an administered antigen. A modification comprises addition of phosphoethanolamine (PEtN) groups to the 1- and/or 4' phosphates on the lipid A or lipid A-based core (e.g., lipid $IV_A$ and de-O-acyl lipid A cores) of the molecule. The PEtN groups are linked to one or both phosphate(s) of the lipid A or lipid A-based molecules (e.g., lipid $IV_A$ and de-O-acyl lipid A molecules) via a phospho-anhydride bond. In an embodiment, the PEtN-modified saccharide(s) (e.g., PEtN-LPS molecules) of this disclosure retain TLR4 binding activity resulting in production of cytokines and an enhancement in immune responses. PEtN-modified saccharide (e.g., modified LPS molecules) of the present disclosure exhibit reduced toxicity.

This disclosure also provides modified lipid A and lipid A-based compounds (e.g., lipid $IV_A$ and de-O-acyl lipid A compounds) that act as vaccine adjuvants to enhance immune responses to an administered antigen. The lipid A and lipid A-based compounds (e.g., lipid $IV_A$ and de-O-acyl lipid A compounds) of this disclosure have reduced toxicity due to the addition of phosphoethanolamine (PEtN) groups to the 1- and/or 4' phosphates on the backbone of the molecules. The PEtN groups are linked to phosphates of the lipid A and lipid A-based compounds (e.g., lipid $IV_A$ and de-O-acyl lipid A compounds) via a phosphoanhydride bond. In an embodiment, the PEtN lipid A and lipid A-based compounds (e.g., lipid $IV_A$ and de-O-acyl lipid A compounds) of this disclosure retain TLR4 binding activity resulting in production of cytokines and an enhancement in immune responses.

In an aspect, the present disclosure provides PEtN-modified saccharide(s) (e.g., compound) and PEtN-LPS molecules.

In an aspect, the present disclosure provides compositions. The compositions may comprise pharmaceutically acceptable carriers. The compositions may be immunogenic and/or vaccine compositions.

In an aspect, the present disclosure provides methods of using compounds and compositions of the present disclosure. The methods may be used to generate and/or enhance an immune response in an individual.

In an aspect, this disclosure provides a kit comprising an administration device suitable for administration and an immunogenic formulation comprising an adjuvant and an antigen as described herein. In another aspect, this disclosure provides a kit comprising separate formulations of the adjuvant and the antigen. These separate formulations may be mixed together and administered to an individual or they may be administered separately. The device may be supplied pre-filled with the immunogenic formulation. In one embodiment, the immunogenic formulation is in a liquid volume smaller than for conventional intramuscular vaccines. For example, the intramuscular administration devices may contain a volume of between about 0.05 ml and 5.0 ml. The kit may also contain a needle delivery device suitable for the appropriate administration route.

BRIEF DESCRIPTION OF THE FIGURES

For a fuller understanding of the nature and objects of the disclosure, reference should be made to the following detailed description taken in conjunction with the accompanying figures.

ΔeptAΔgutQΔkdsDΔlpxLΔlpxMΔlpxPΔpagP+pEptA) was
incubated for 48 hours at 37° C. in MOPS-Tris buffer [100
μg/ml substrate, 50 mM MOPS/50 mM Tris (adjusted to pH
6.5, 7.4, or 8.5), 100 mM NaCl, 1 mM MgCl$_2$, 20 μM
ZnCl$_2$), and then treated with cIAP (10 U/ml cIAP) to
release inorganic phosphate from spontaneously hydrolyzed
PEtN. Phosphate was quantified using the malachite green
assay. (D) Lipid IV$_A$ species were hydrolyzed for 48 hours
in MOPS-Tris buffer at the indicated pH as described in (C)
except samples were isolated by extraction before separation
by TLC. Total lipid was visualized by sulfuric acid charring.

Figure 5:
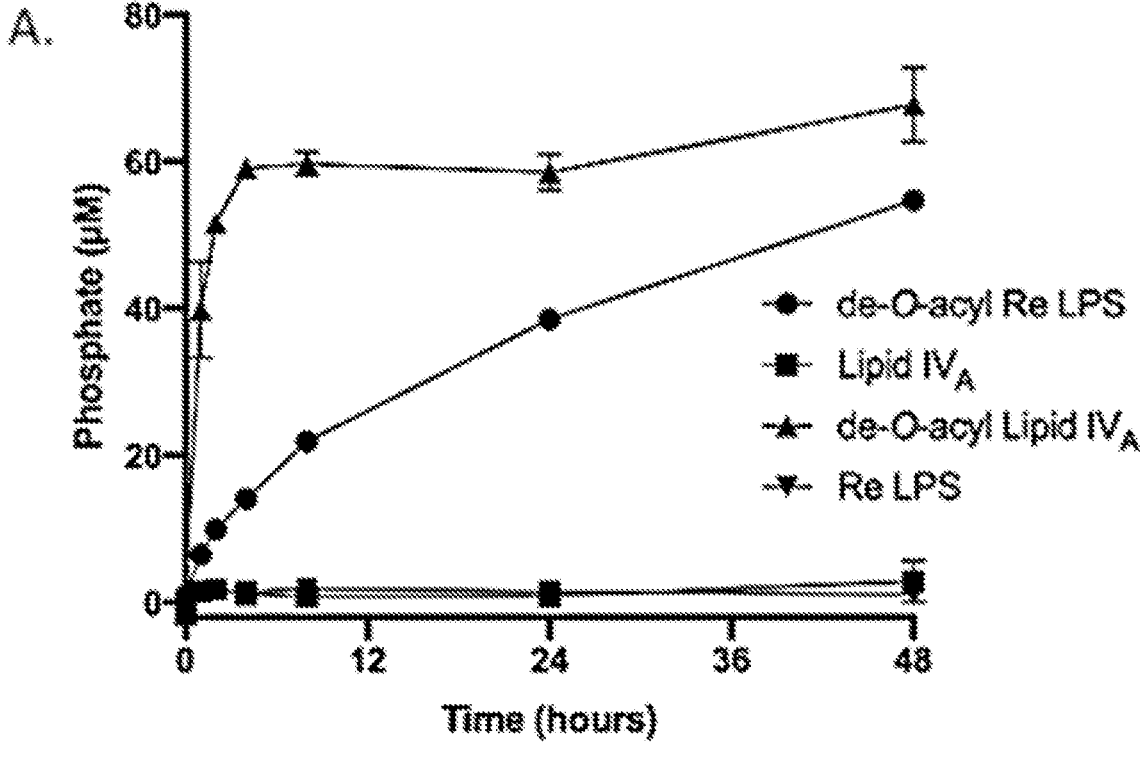
Figure 5:
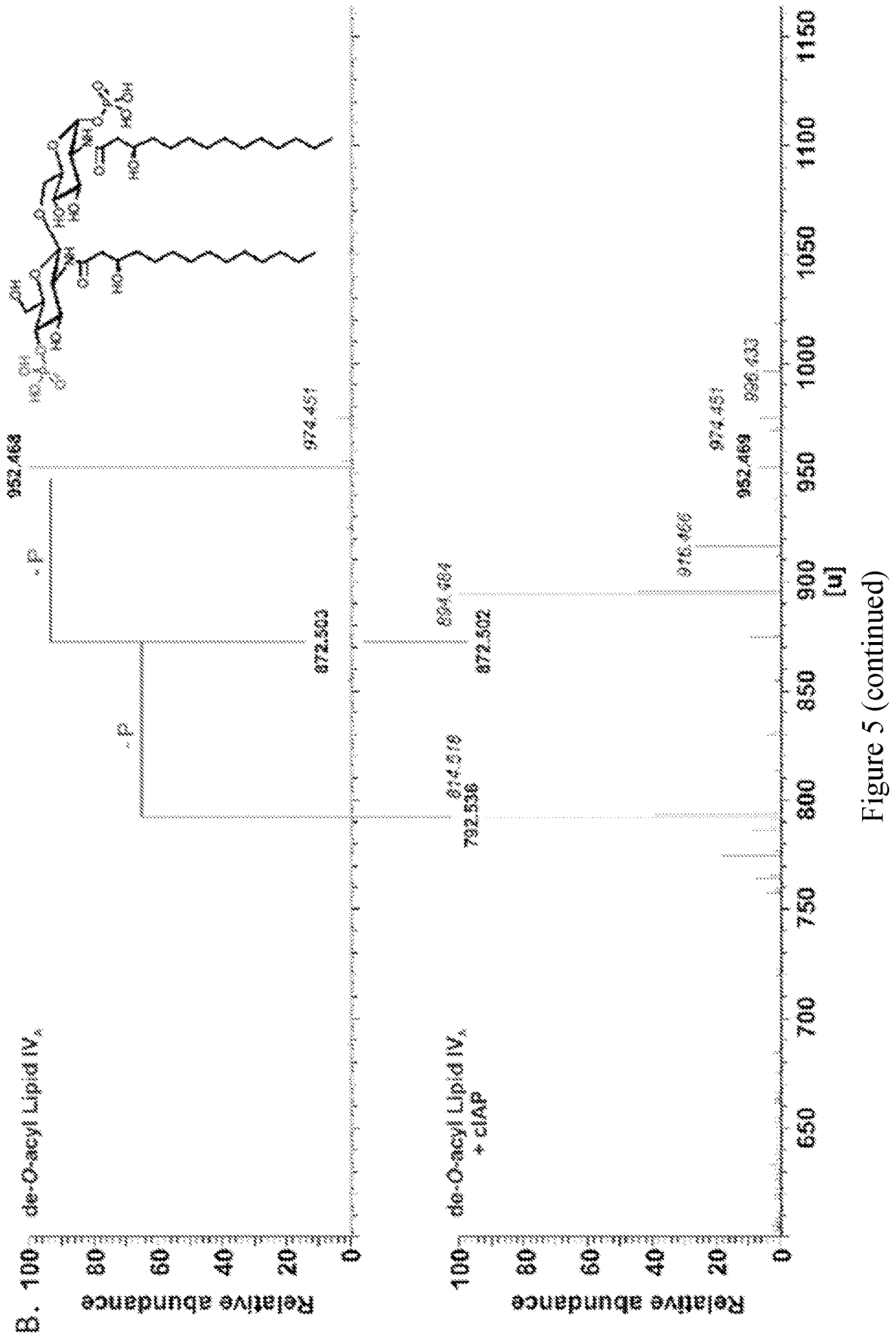
Figure 5:
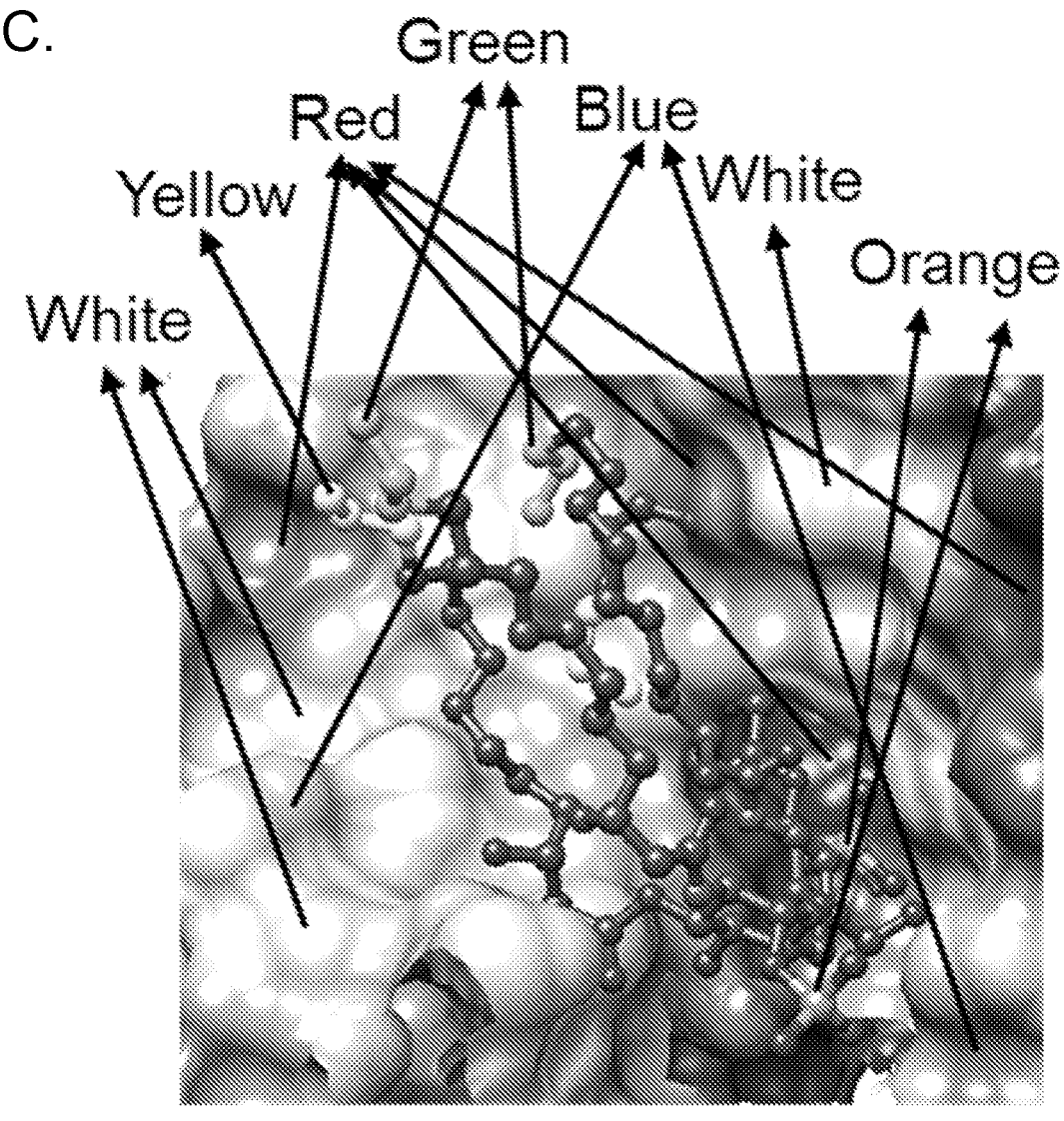
Figure 11:
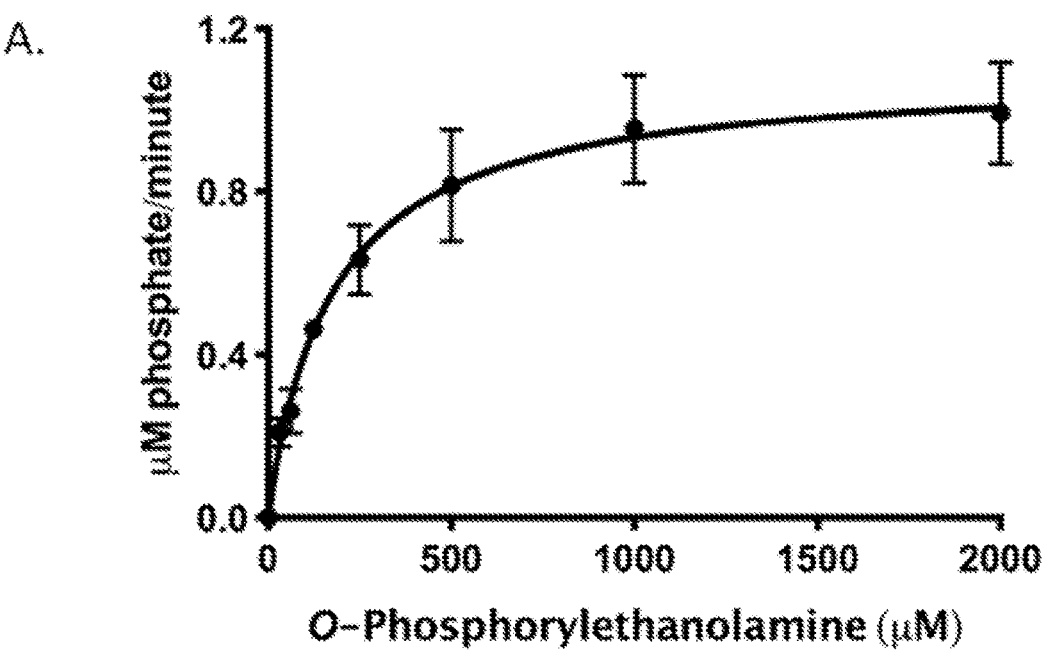
Figure 11:
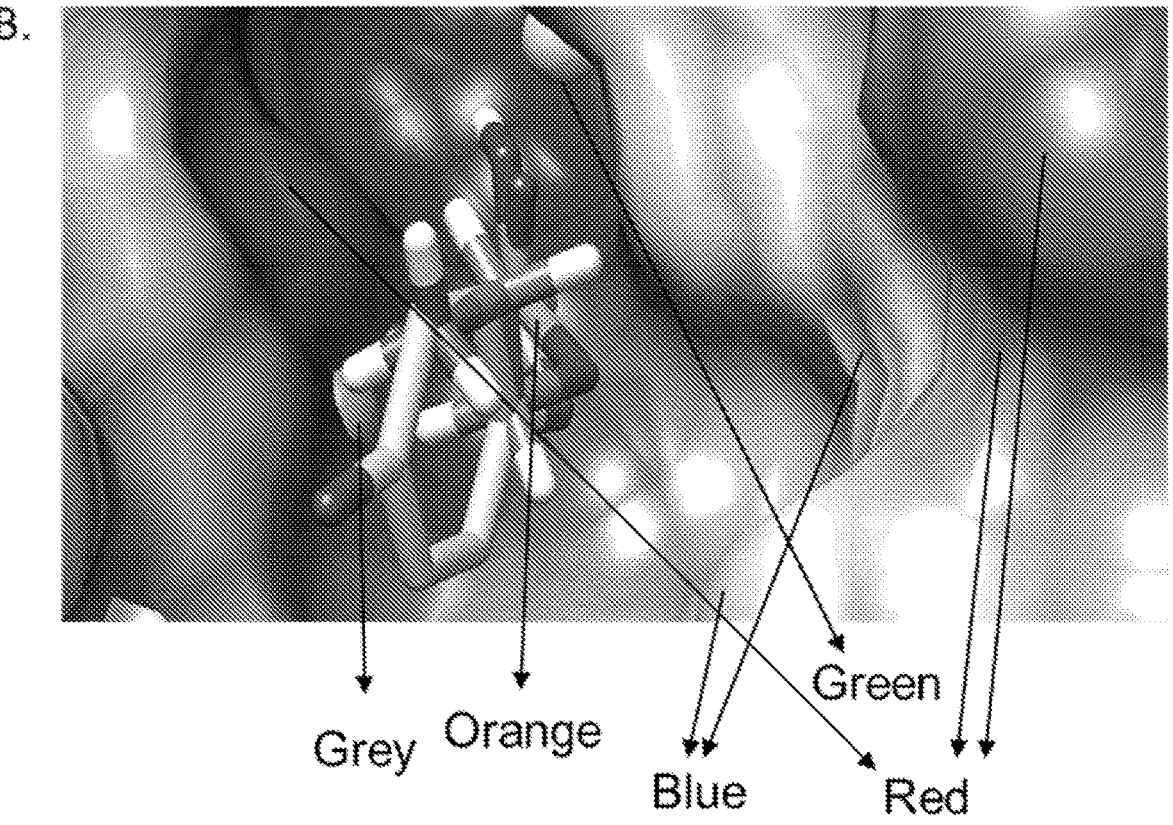

FIG. 5 shows de-O-acylated lipid A is rapidly dephos-
phorylated by cIAP. (A) Phosphate released by cIAP from
either de-O-acylated lipid IV$_A$ or Re LPS (100 μg/ml sub-
strate, 4 U/ml cIAP, 50 mM Tris-HCl (pH=7.4), 100 mM
NaCl, 1 mM MgCl$_2$, 20 μM ZnCl$_2$) at 37° C. was quantified
at the indicated times using the malachite green assay. The
data is plotted as the mean±SD of three independent repli-
cates. (B) MS analysis in the positive anion mode of
de-O-acyl lipid IV$_A$ before (top panel, calculated mass
952.467 u; recorded in negative ion mode) and after treat-
ment with cIAP (bottom panel, calculated masses of 872.501
u and 792.535 u for monophosphoryl and non-phosphory-
lated products, respectively; recorded in positive ion mode).
The highly cIAP susceptible phosphate at C4'-GlcNII is
colored orange. Masses resulting from dephosphorylation
events are indicated (P), while masses in italic style repre-
sent sodium adducts (Δm=22 u). (C) Binding model of
tetra-acylated lipid IV$_A$ with the C4'-GlcNII phosphate at the
active site of cIAP. The phosphorylated catalytic serine
covalent intermediate (bottom-right, deeply buried in the
cleft) is aligned with the C4'-GlcNII lipid IV$_A$ phosphate as
reference (FIG. 11). Proximal atoms of the two O-acylated
side chains (with the terminal Ω, Ω-1, Ω-2 carbon atoms
colored in yellow) permeate the protein surface. The two
N-acylated side chains can occupy the cleft in their entire
length without any steric clashes (green caps). The anomeric
1-phosphate group of GlcNI lies to the front (bottom most,
right) and is only slowly cleaved in de-O-acyl lipid A
(N,N-di-acylated lipid IV$_A$ derivative, modeled in FIG. 13).
Red, blue, and white surface colors indicate negative, posi-
tive, and neutral partial charges, respectively. Hydrogen
atoms are not displayed.

Figure 6:
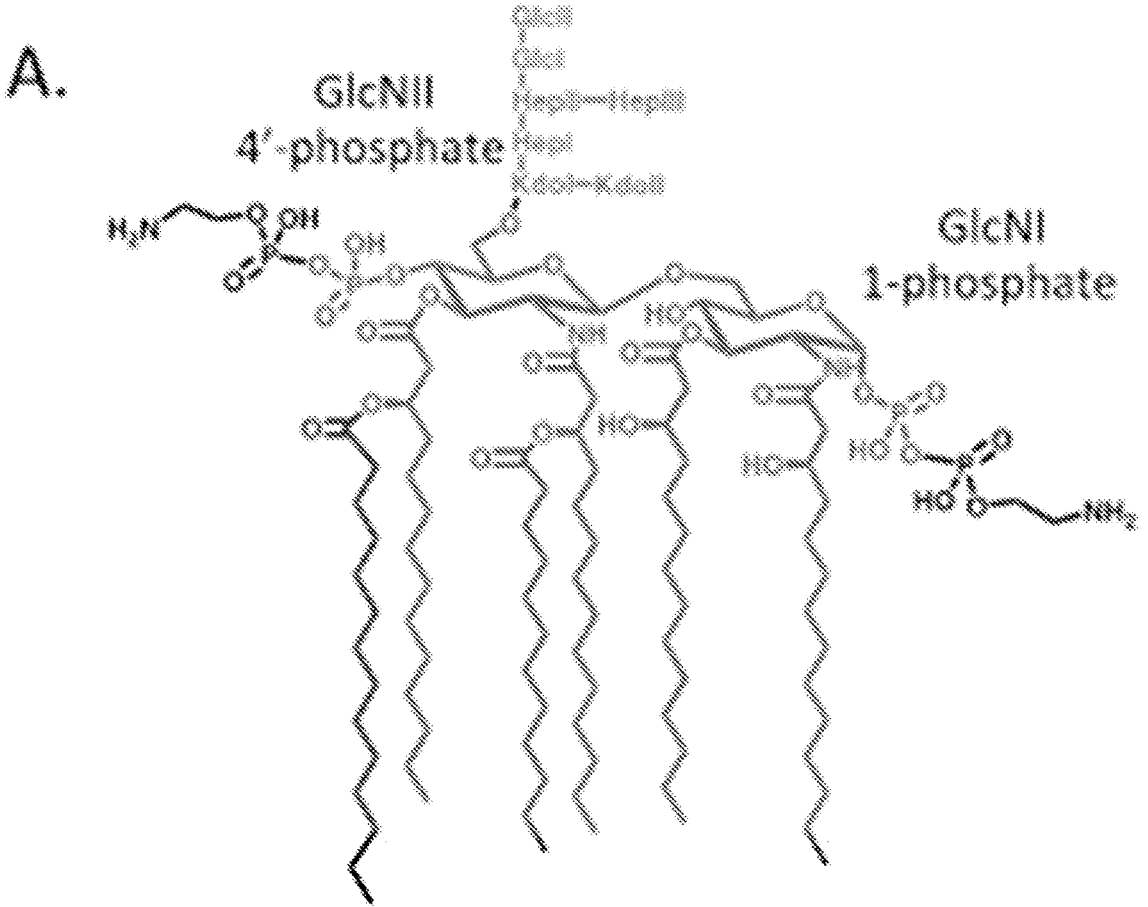
Figure 6:
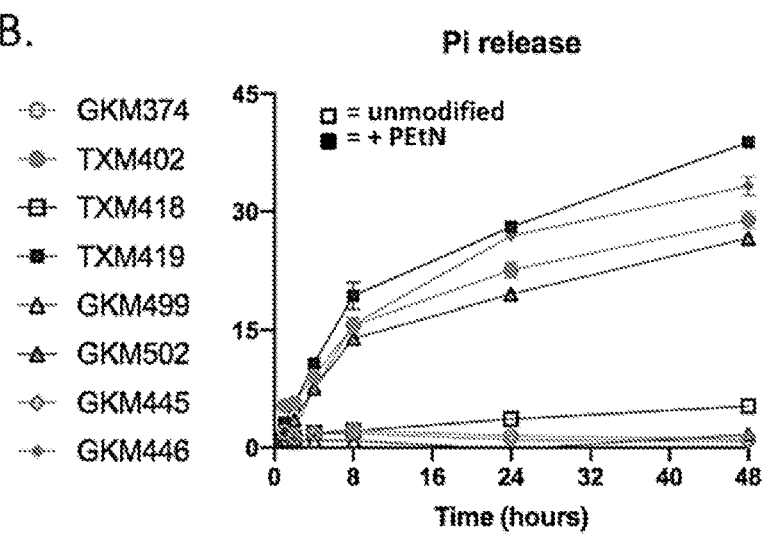
Figure 6:
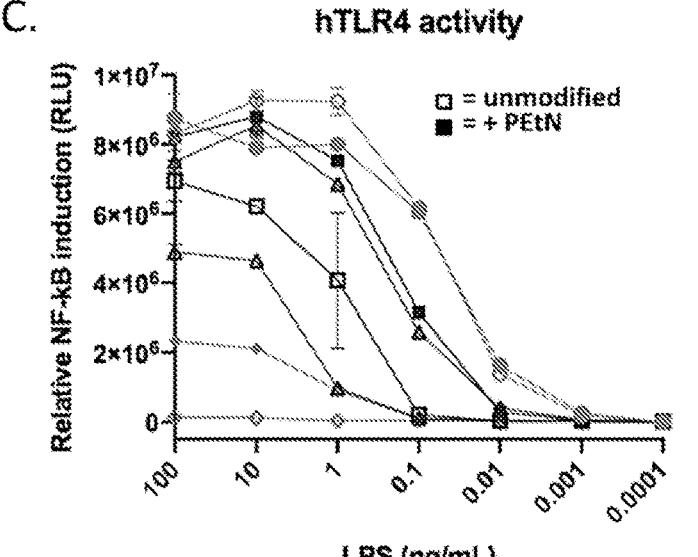
Figure 6:
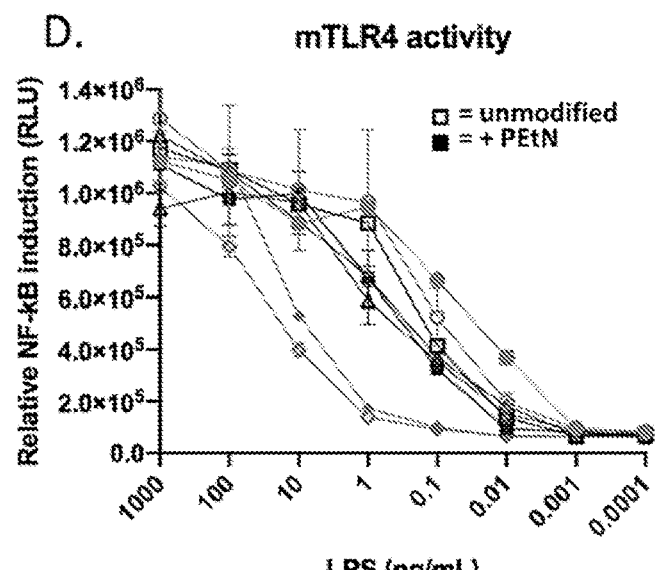

FIG. 6 shows LPS modification with PEtN by EptA
induces NF-κB activity through hTLR4/MD2 signaling. (A)
The structure of hexa-acylated lipid A modified with PEtN
at both the C1-GlcNI and C4'-GlcNII phosphates. The major
lipid A acylation chemotype being produced in paired
pEptA$^{-/+}$ *E. coli* constructs GKM374/TXM402
(ΔeptAΔarnAΔeptC), TXM418/TXM419
(ΔeptAΔarnA≠eptCΔlpxM), GKM499/TXM502
(ΔeptAΔarnAΔeptCΔlpxLΔlpxMΔpagP), and ClearColi®
K-12 GKM445/GKM446
(ΔeptAΔgutQΔkdsDΔlpxLΔlpxMΔlpxPΔpagP) are indi-
cated. (B) The inorganic phosphate released during incuba-
tion with cIAP [4 U/ml, 100 μg/ml substrate, 50 mM
Tris-HCl (pH=8.25), 100 mM NaCl, 1 mM MgCl$_2$, 20 μM
ZnCl$_2$] was measured using the malachite green assay. Data
are representative of three independent experiments done in
duplicates and the error bars show SDs. (C) HEK293/
hTLR4-MD2-CD14 NF-κB reporter cells were stimulated
with the indicated LPS chemotypes and the luciferase activ-
ity was measured. (D) The bioactivity of the LPS chemo-
types with murine TLR4/MD2 receptor was re-tested using
stably transfected HEK293/mTLR4-MD2-CD14 reporter
cells. For both hTLR4 and mTLR4 assays, data are representative of three independent experiments conducted in duplicates with the error bars showing SDs.

Figure 7:
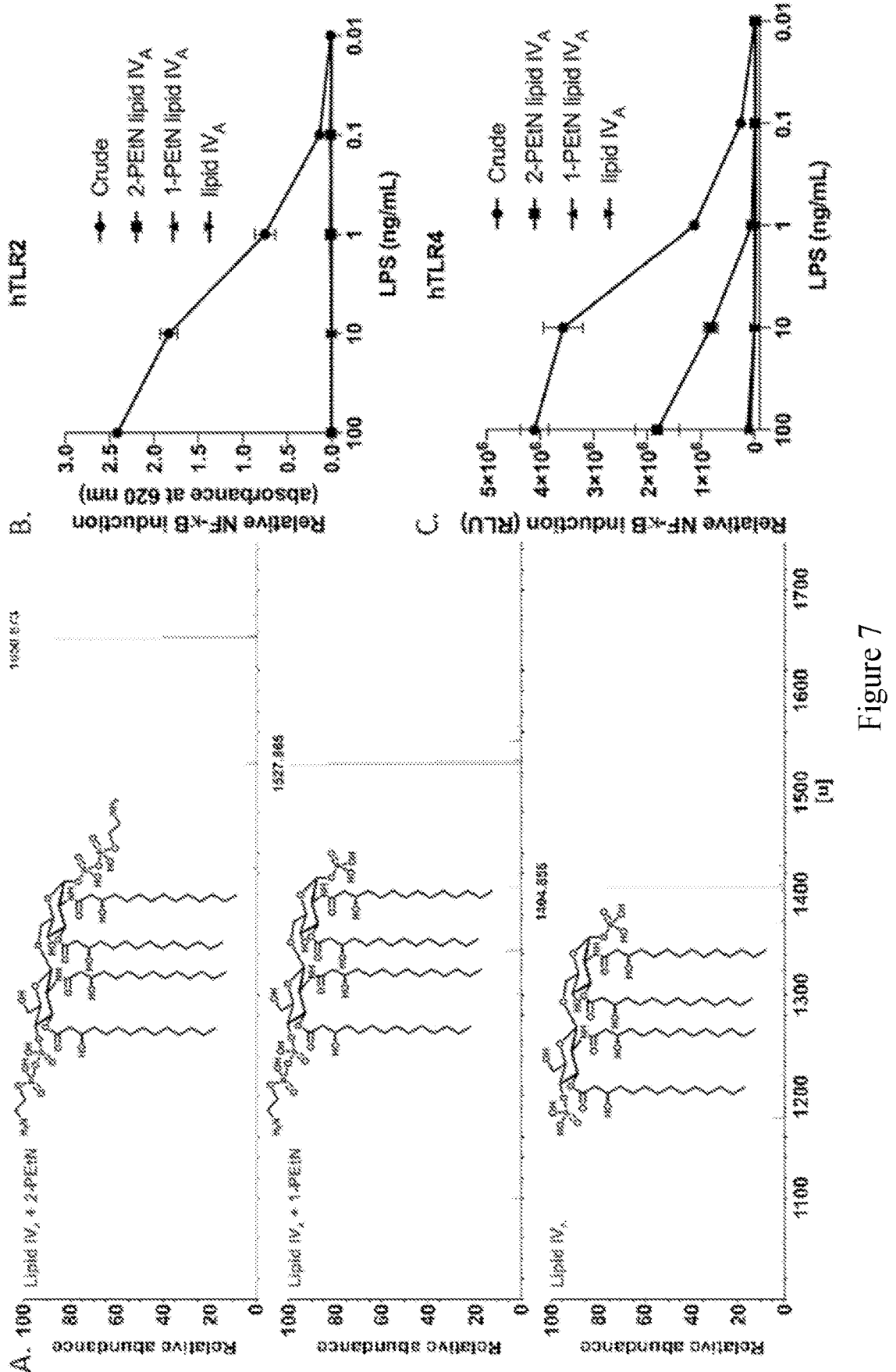

FIG. 7 shows MS analysis and TLR activity of purified 2-PEtN and 1-PEtN modified lipid $IV_A$ samples. (A) MS analysis of the purified PEtN-lipid $IV_A$ species isolated from *E. coli* strain TXM844 (msbA148ΔeptAΔgutQΔkdsDΔlpxLΔlpxMΔpagPΔlpxP+ pEptA). (B) Relative NF-κB induction in HEK-Blue hTLR2 reporter cells stimulated with crude LPS, 2-PEtN lipid $IV_A$, 1-PEtN lipid $IV_A$, and unmodified lipid $IV_A$. Data are from experiments done in triplicate and the error bars show SDs. (C) Relative NF-κB induction in HEK293/hTLR4-MD2-CD14 reporter cells stimulated with crude PEtN-lipid $IV_A$ (TXM844) and the purified 2-PEtN lipid $IV_A$, 1-PEtN lipid $IV_A$, and unmodified lipid $IV_A$ fractions. Data are from experiments conducted in triplicate and the error bars show SDs.

Figure 8:
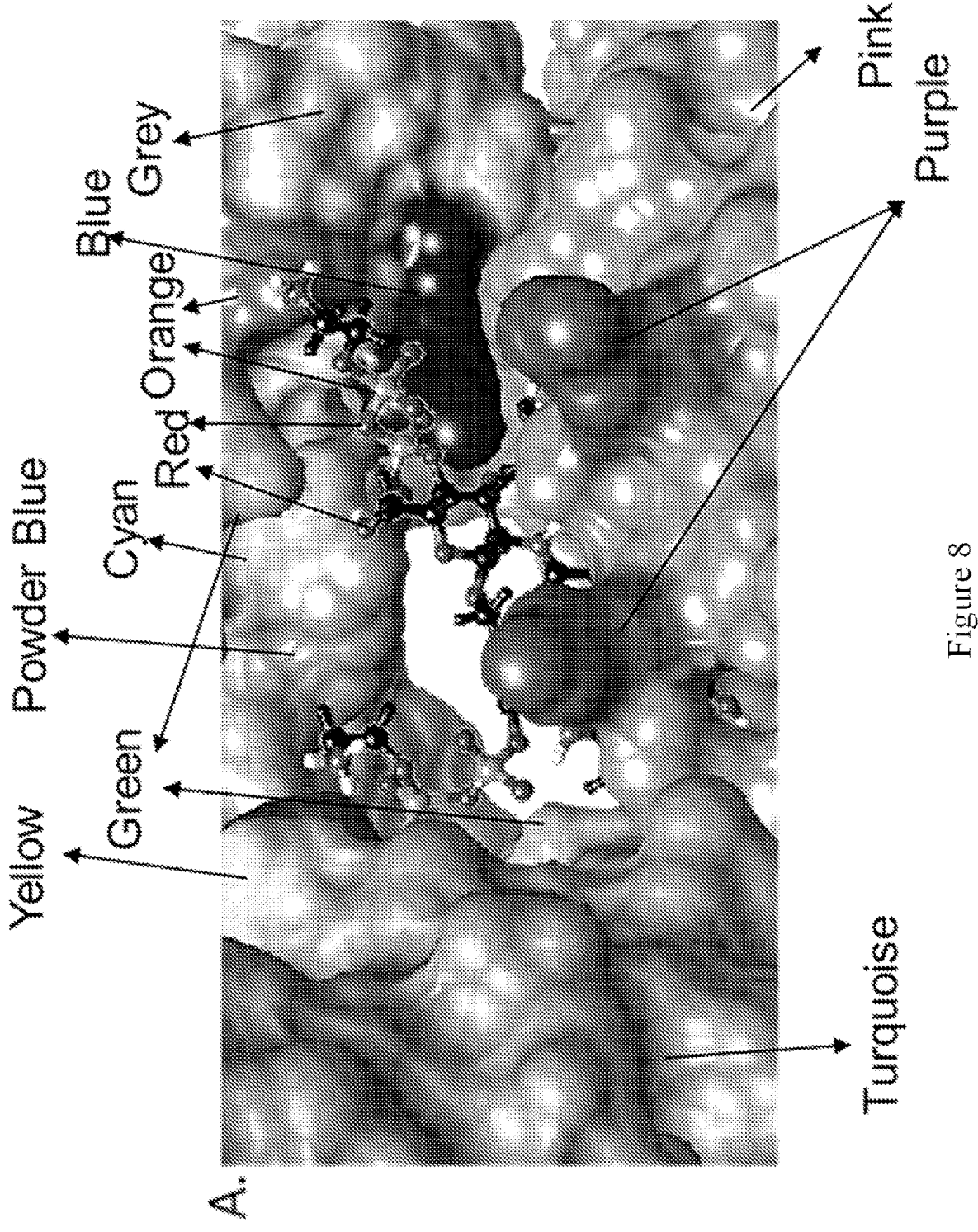
Figure 8:
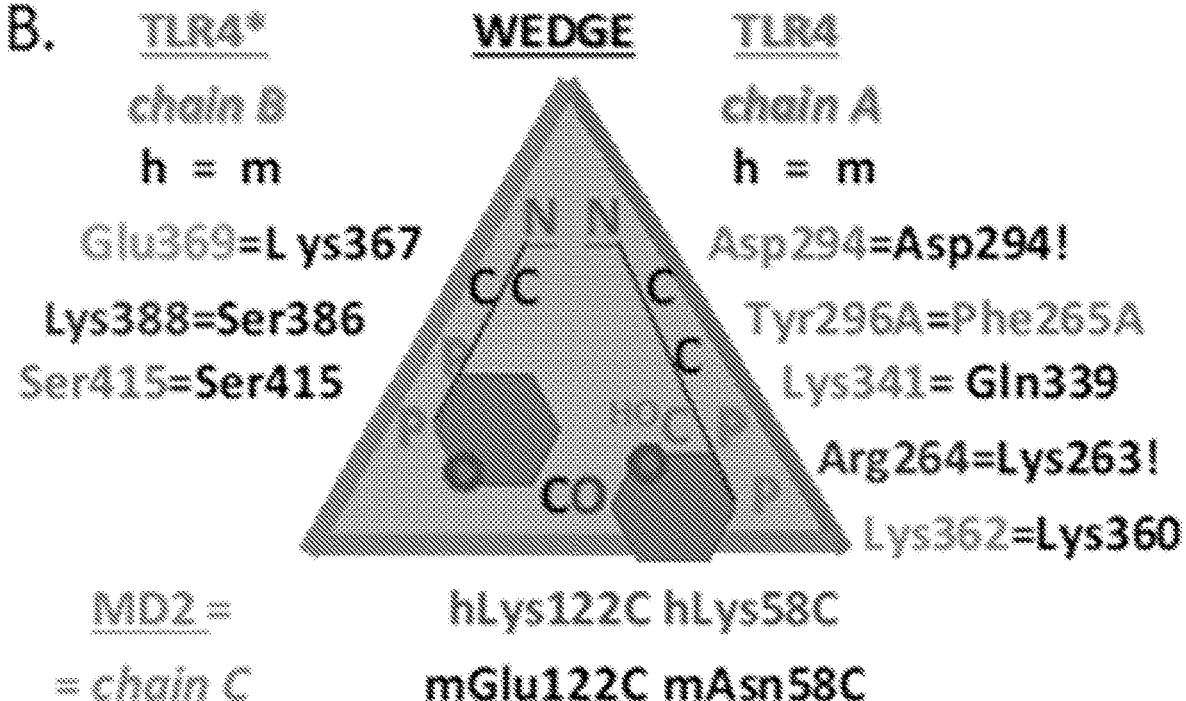

FIG. 8 shows simulated hTLR4/MD2 binding of 2-PEtN modified lipid $IV_A$. (A) Computational model of hTLR4/MD2 with 2-PEtN modified lipid $IV_A$ substrate bound at the hTLR4 homodimer interface. Surface color codes are grey for TLR4 (A chain, right), turquoise for the second TLR4* subunit (B chain, left), and pink for MD2 (C chain, bottom). Key substrate binding determinants on each subunit chain are indicated as follows. For MD2, hLys122C and Lys58C (right) are indicated by two purple patches. Patches on TLR4* to the left highlight hGlu369B (yellow, equivalent to mLys367B), hLys388B (blue, behind hGlu369B), and hSer415B (green, below hGlu369B). Mid section patches on TLR4 are hLys362A (powder blue) and hLys341A (cyan) are highlighted, while top right side patches include hTyr296A (green), hAsp294A (orange), and hArg264A (blue). The GlcNII ring is visible in the cleft while the GlcNI moiety is occluded by hLys122C. The two cationic $H_3N^+$-head groups of PEtN contact anionic hGlu369B (anomeric C1-phosphate of GlcNI) and hAsp294A (non-anomeric C4'-phosphate of GlcNII). The MD2 lipophilic cavity buries all four acyl chains of lipid $IV_A$. Tyr296 is positioned to contact the 6'-C—OH group or the 4'-pyrophosphate group of PEtN on GlcNII. (B) Binding map schematic highlighting critical residues that vary between the human and murine TLR4/MD2 receptor complex. To bind LPS-like ligands, the dimerized receptor complex provides a binding site contoured by TLR4*/MD2/TLR4. When projected onto a plane from a certain perspective, the three proteins (B/C/A chains) form a triangle (wedge). Amino acids potentially serving as favorable electrostatic contact points for the cationic amino head groups of PEtN moieties are noted, including the anionic hAsp294 (TLR4) and hGlu369 (TLR4*) residues. Note, the latter is replaced by a non-homologous lysine (mLys367B) residue in the mTLR4 receptor. As in panel (A), hTyr296 (green) is interacting with the C6-OH group of GlcNII (green) or with the adjacent pyrophosphate group (orange). Atom colors for the 2-PEtN modified lipid $IV_A$ ligand: black C—H, orange P, red O, blue N, white polar H.

Figure 9:
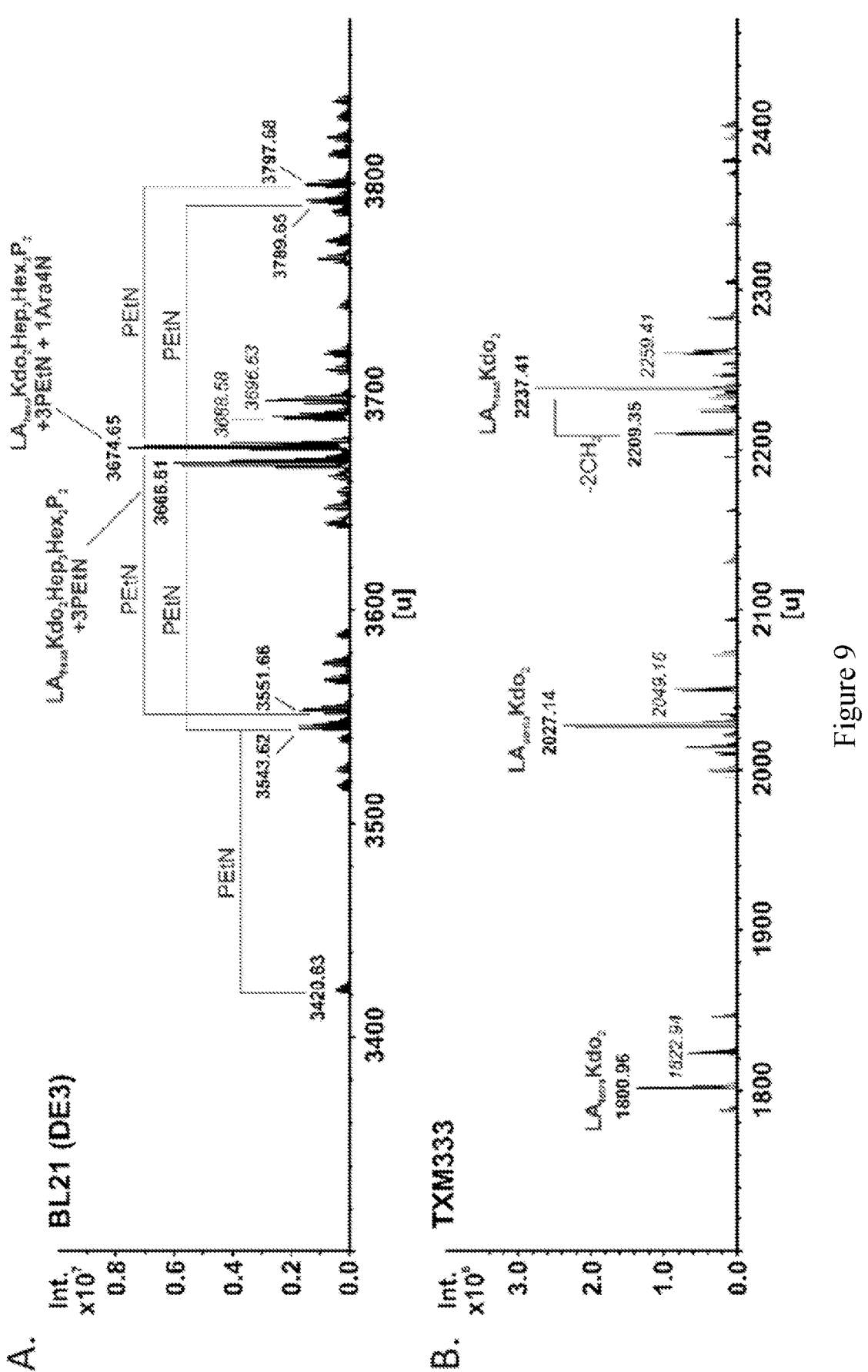

FIG. 9 shows MS spectra of wildtype *E. coli* BL21 (DE3) LPS (A) and unmodified Re LPS from TXM333 (ΔlpcAΔeptAΔarnA) (B). Masses in italic style denote sodium adducts (Δm=22 u). Mass shifts due to nonstoichiometric phosphoethanolamine (PEtN) substituents are indicated (Δm=123 u). Chemical compositions are assigned in Table 1.

Figure 10:
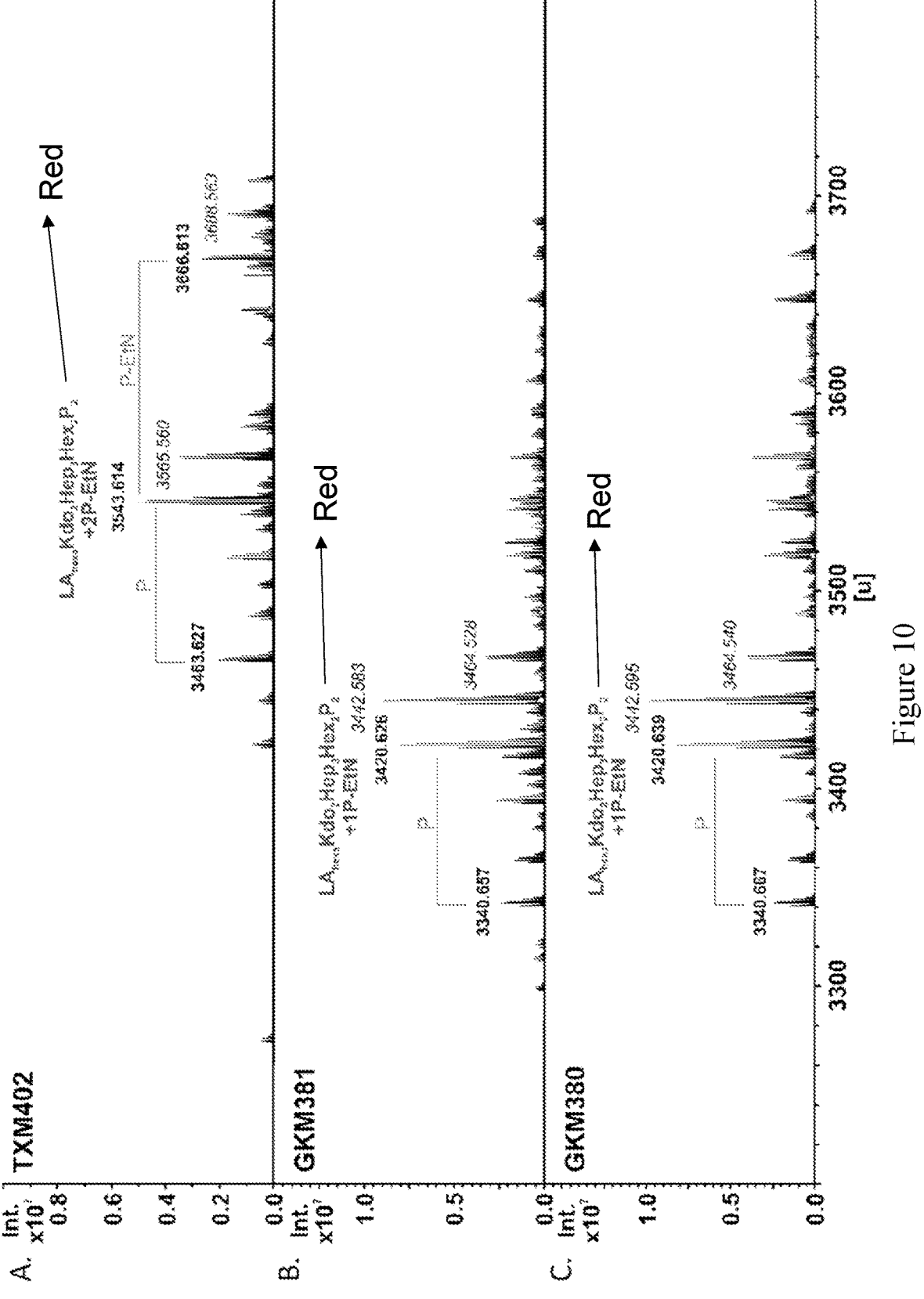
Figure 10:
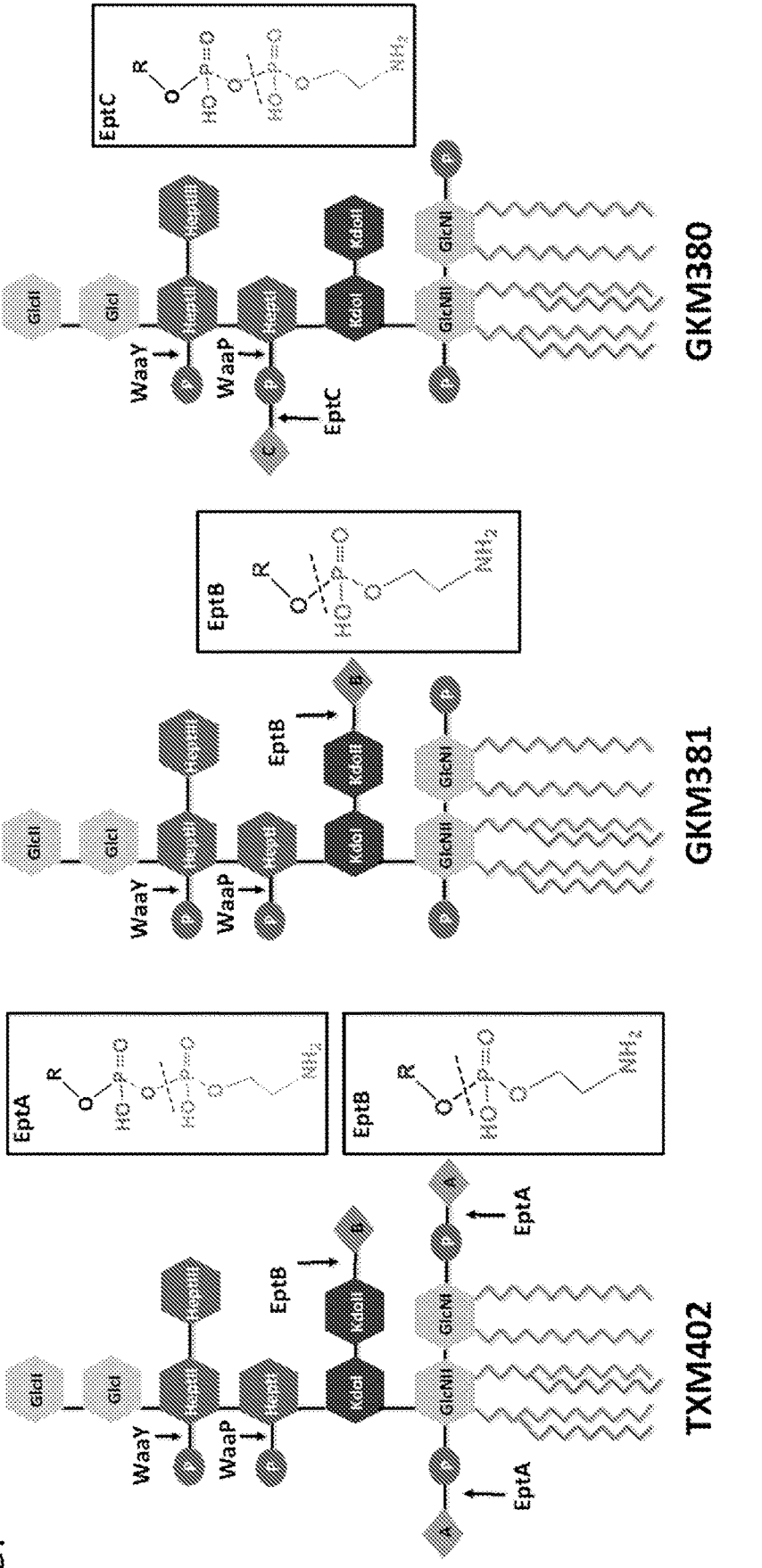

FIG. 10 shows MS spectra from *E. coli* strains constitutively expressing pEptA in TXM402 (A), pEptB in GKM381 (B), or pEptC in GKM380 (C). Masses in italic style denote sodium adducts (Δm=22 u). Mass shifts due to nonstoichiometric phosphate (Δm=80 u, P) and phosphoethanolamine (Δm=123 u, PEtN) are indicated. The chemical composition of the predominant LPS glycoform in each strain is in red type, with the respective structural schematics depicted in panel (D). LA=lipid A.

FIG. 11 shows O-Phosphorylethanolamine (O-PEtN) is a substrate for cIAP. (A) The rate of inorganic phosphate released by cIAP (0.04 U/ml) as a function of O-PEtN substrate concentration was measured using the malachite green assay. Data was fit using the standard Michaelis-Menten equation ($K_m$ of 173±27 μM for O-PEtN and $V_{max}$ of 1.09±0.05 μM/min). Data are plotted as an average of two independent experiments conducted in duplicates with error bars showing SDs. (B) Display of O-PEtN at a mammalian AP active site. The surface was computed for rat IAP (4KJD.pdb, 4KJG.pdb). While the PEtN position was computed, the phosphate and phenol fragment (a substrate analog) take their locations from observed phosphatase co-crystal structures. They were merged into all models as reference to validate the computed poses of equivalent mono-phosphorylated glucosamine rings of lipid A (see FIG. 5C and FIG. 13). Stick colors: orange P, red O, blue N, yellow C of para-nitro-phenol (substrate analog) and white H and magenta C atoms of PEtN. Surface colors reflect positive (blue) or negative (red) partial charges from functional residue groups. More nonpolar (neutral, mostly aliphatic) zones of amino acids show fading colors while deeper blue or red colors symbolize increasing positive or negative charge densities. Smaller bright and dark shading imitate light reflection and shadows in space for three-dimensional impression. Two of the three metal ions are partially visible (grey: $Zn^{2+}$, green $Mg^{2+}$). The locations of the cleavage sites of EcAP (5TJ3.pdb) and rat IAP (4KJD.pdb) can be brought on the same footage guided by the superposition of their phosphates and catalytic residues (not displayed).

Figure 12:
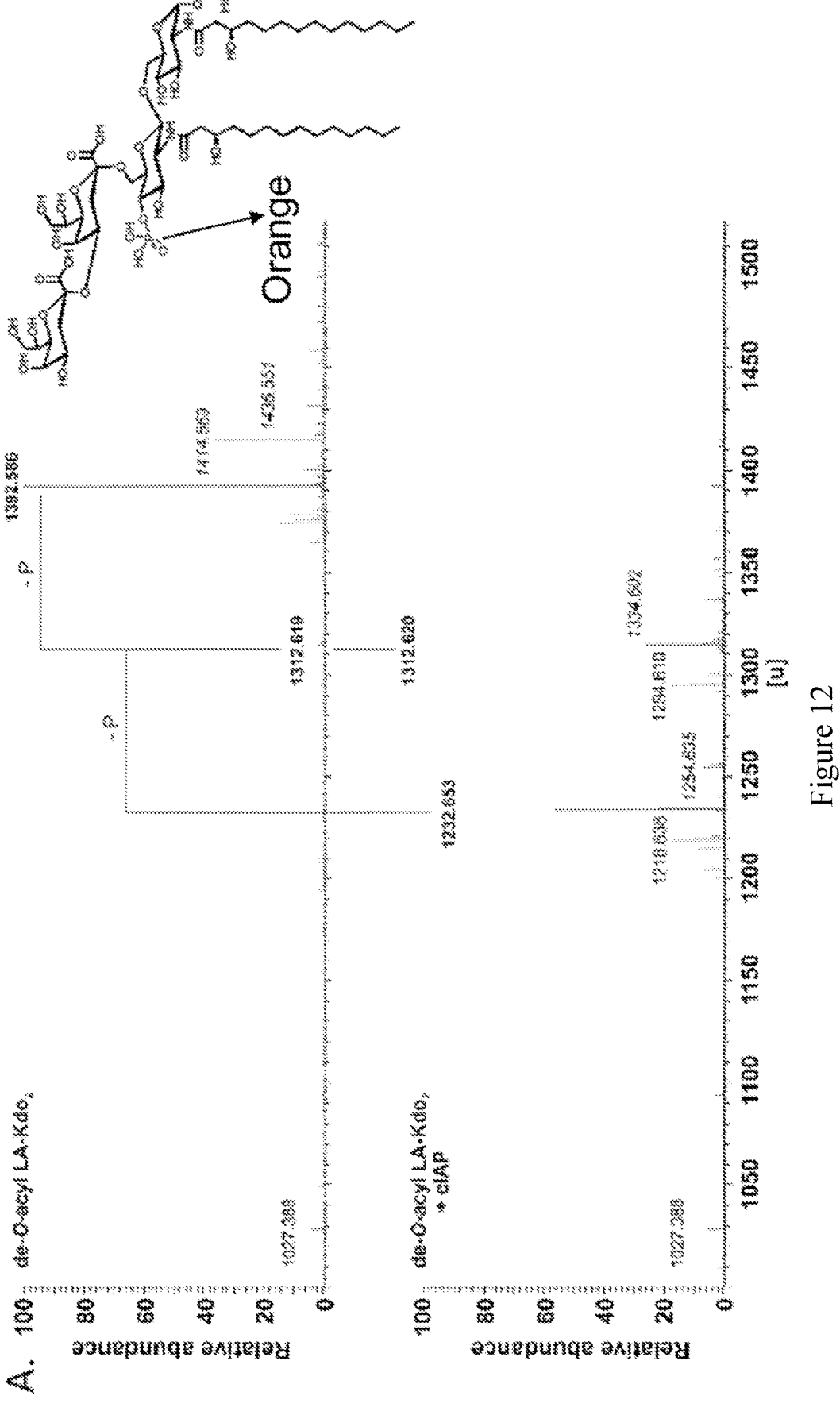
Figure 12:
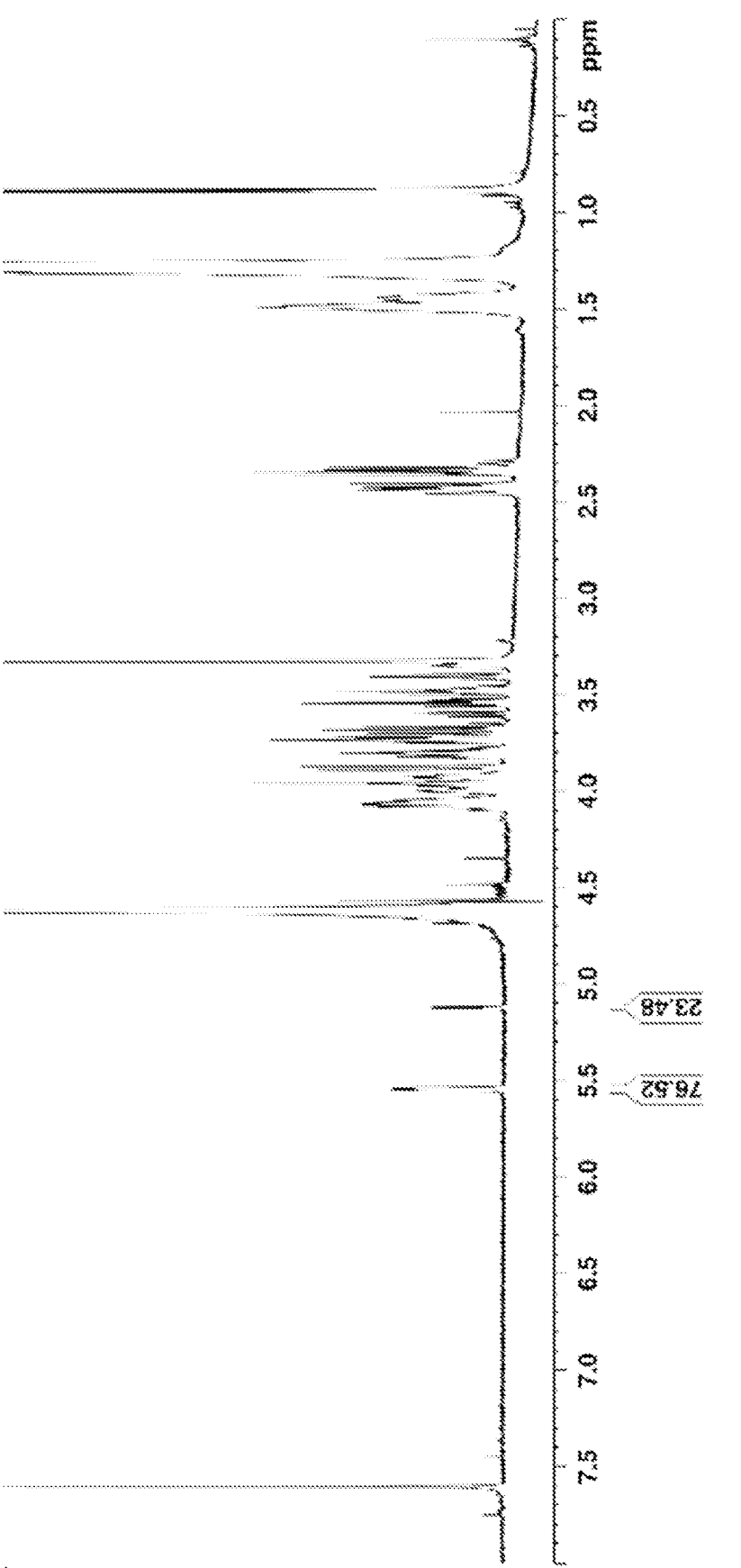

FIG. 12 shows de-O-acylated lipid A substrates are dephosphorylated by cIAP. (A) MS analysis in the negative ion mode of de-O-acyl Re LPS before (top panel, calculated mass 1392.584 u) and after treatment with cIAP (bottom panel, calculated masses of 1312.618 u and 1232.651 u for monophosphoryl and non-phosphorylated products, respectively). The more cIAP-susceptible phosphate at C4'-GlcNII is colored orange. Masses resulting from dephosphorylation events are indicated (P), while masses in italic style represent sodium adducts (Δm=22 u). (B) $^1H$ NMR analysis of cIAP products from de-O-acyl lipid A that had been prepared from ClearColi® BL21 (DE3) (TXM843). Integration of the downfield α-anomeric proton signals indicates that the majority (~77%) of the monophosphoryl products retain the GlcNI phosphate ($δ_H$ 5.54 ppm). The O-1-dephosphorylated GlcNI is represented by the doublet for H1 at $δ_H$ 5.12 ppm. LA=lipid A.

Figures 13, 14:
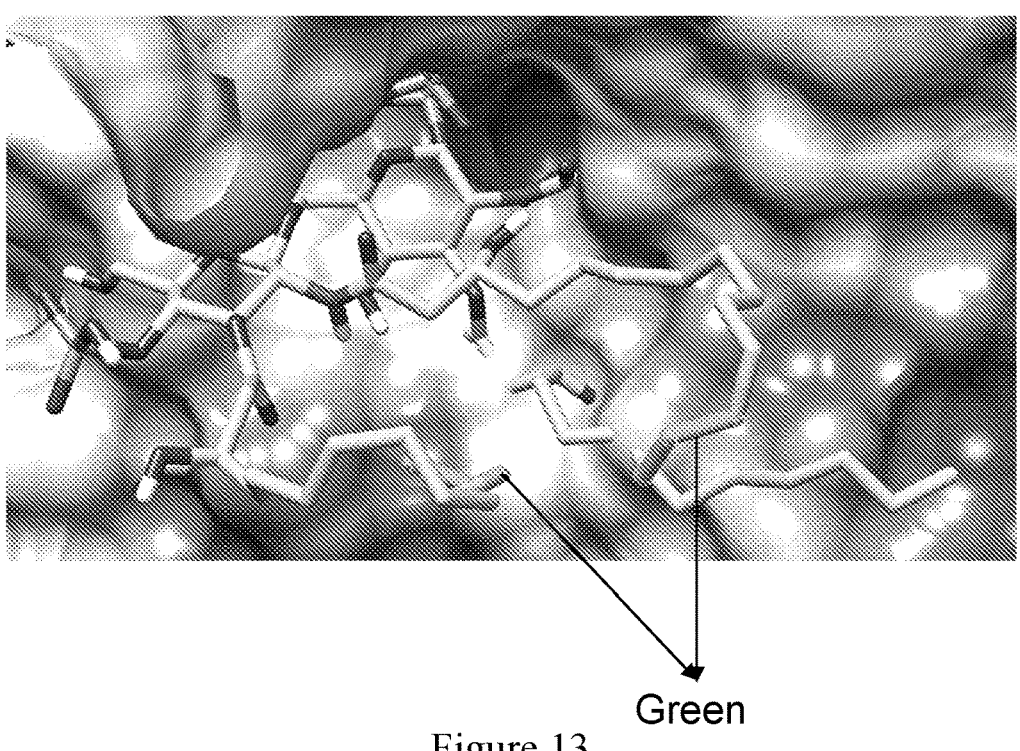

FIG. 13 shows a stick model of tetra-acylated lipid $IV_A$ with the anomeric C1-GlcNI phosphate group positioned in the cIAP catalytic cleft. The phosphorylated catalytic serine covalent intermediate is included for reference (topmost deeply buried in the cleft). In this orientation, both acyl groups (ester and amide linked) on GlcNI of lipid $IV_A$ will clash with the protein surface if the anomeric phosphate is appropriately positioned for cleavage. In contrast, a di-acylated derivative with only the two acyl side chains on GlcNII (terminal Ω, Ω-1, Ω-2 carbon atoms colored in green) could occupy the active site without steric hindrance.

FIG. 14 shows pre-incubation in buffer of increasing pH reduces hTLR4 agonist activity for PEtN-modified lipid $IV_A$. Relative NF-κB induction in HEK293/hTLR4-MD2-CD14 cells stimulated with lipid $IV_A$ [GKM445 ClearColi®

K-12 (ΔeptAΔgutQΔkdsDΔlpxLΔlpxMΔlpxPΔpagP)] or PEtN-modified lipid $IV_A$ [GKM446 (ΔgutQΔkdsDΔlpxΔlpxMΔlpxPΔeptA, pEptA) that had been pre-incubated for 48 hours at 37° C. in MOPS/Tris buffer at pH 6.5, 7.4, or 8.5. Data are representative of three independent experiments performed in duplicates with the error bars showing SDs.

Figure 15:
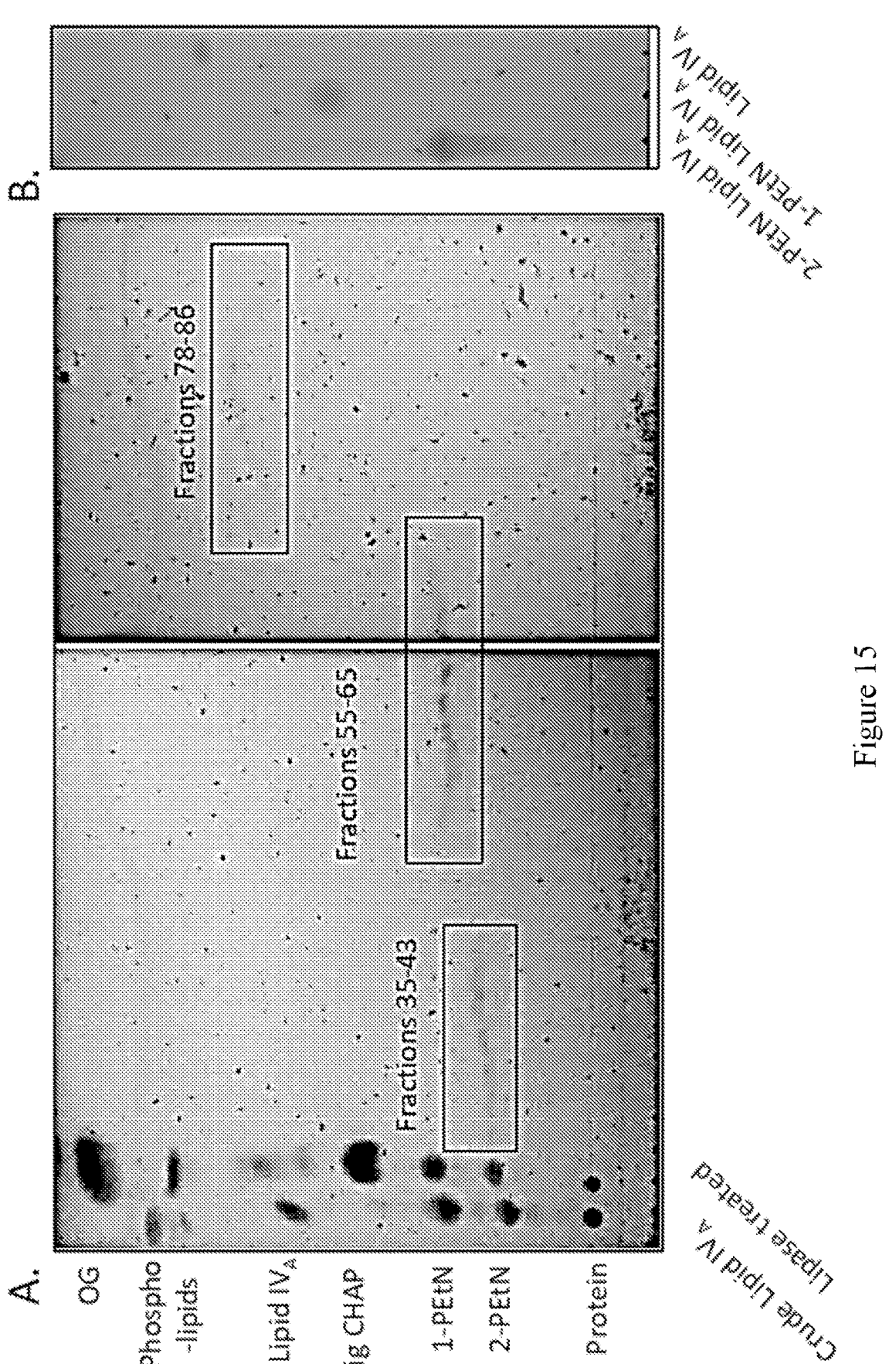

FIG. 15 shows purification of individual PEtN-lipid $IV_A$ species from *E. coli* B strain TXM844 by anion exchange chromatography. (A) Crude PEtN-lipid $IV_A$ isolated by PCP extraction was sequentially treated with two rounds of lipase digestion using the nonionic detergents BIG-CHAP and octyl O-D-glucopyranoside (OG). The product was loaded onto a DEAE column, and fractions screened by TLC after visualization by sulfuric acid charring. Fractions corresponding to lipid $IV_A$, 1-PEtN lipid $IV_A$ (1-PEtN), and 2-PEtN lipid $IV_A$ (2-PEtN) were pooled. (B) Pooled fractions were rechromatographed to confirm purity of isolated lipid $IV_A$, 1-PEtN lipid $IV_A$, and 2-PEtN lipid $IV_A$ preparations.

Figure 16:
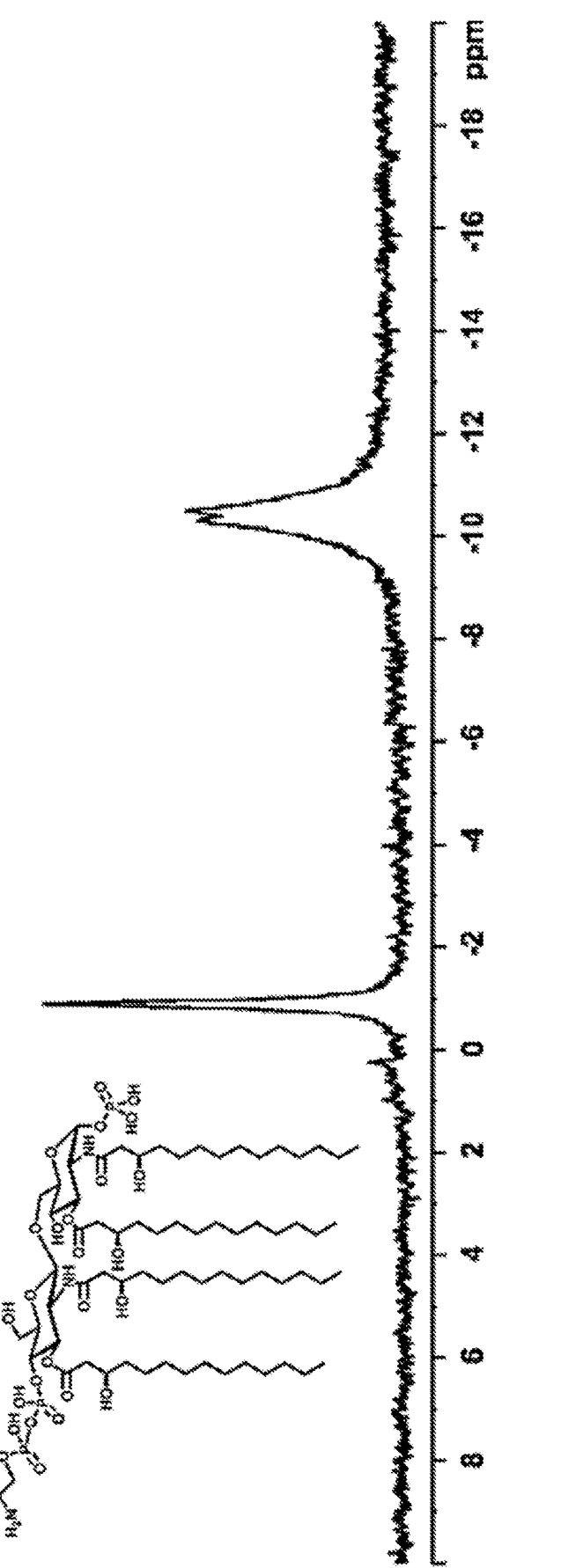

FIG. 16 shows $^{31}$P-NMR analysis of 1-PEtN lipid $IV_A$. The observed signals are in complete agreement with previous assignments for lipid $IV_A$ substituted with a single PEtN residue attached to the C4'-GlcNII phosphate.

Figure 17:
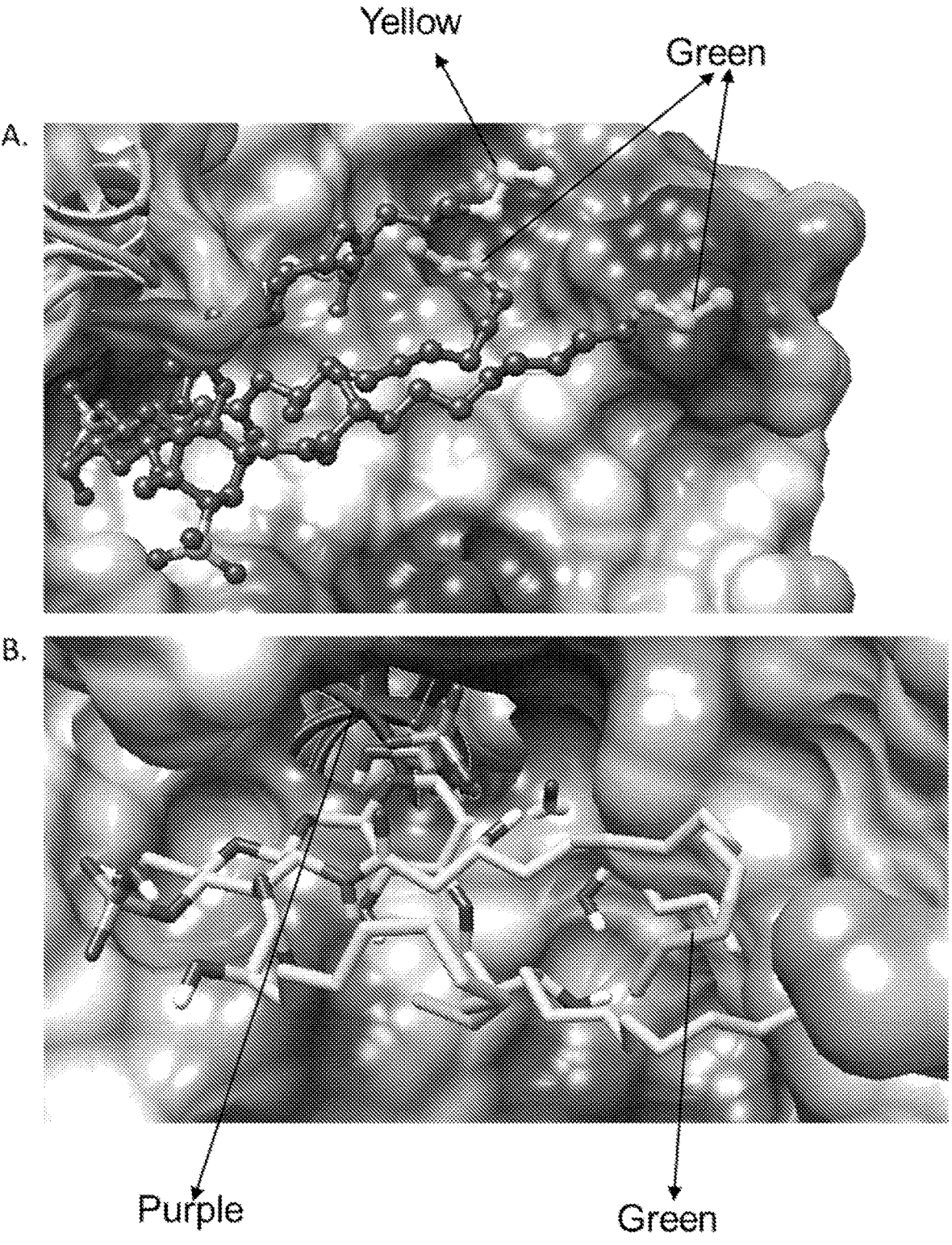

FIG. 17 shows docking of lipid $IV_A$ to bacterial EcAP. (A) Ball and stick model of lipid $IV_A$ with its non-anomeric C4'-GlcNII phosphate group in the bacterial catalytic cleft. The 3D model represents the EcAP crystal structure (1ALK.pdb). The anomeric phosphate group is oriented outwards (foremost bottom, left). In this orientation only both N-acyl side chains (terminal Ω, Ω-1, Ω-2 carbon atoms colored in green) can be accommodated. The adjacent O-linked fatty acids (bottom left between both phosphate groups) are in steric conflict with the protein and permeating the surface so that they remain partially hidden (terminal Ω, Ω-1, Ω-2 carbon atoms colored in yellow). As in the cIAP model (FIG. 5), an N,N-diacylated lipid $IV_A$ congener is predicted to be able to bind and present only its non-anomeric phosphate for cleavage. (B) Stick model of lipid $IV_A$ with its anomeric C1-GlcNI phosphate group in the bacterial active site cleft. In order to be cleaved, the lipid $IV_A$ phosphate must reach the position represented by the reference phosphate (center, top) to be in close proximity to catalytic serine and $Zn^{2+}$ (grey ball in front of purple ribbons). This binding mode is feasible only for a di-acylated lipid $IV_A$ derivative where one N-acyl and one O-acyl chain are attached to GlcNII (terminal Ω, Ω-1, Ω-2 carbon atoms colored green, foreground) because both chains fit into the cleft without being sterically impeded by the protein surface.

DETAILED DESCRIPTION OF THE DISCLOSURE

Although claimed subject matter will be described in terms of certain embodiments/examples, other embodiments/examples, including embodiments/examples that do not provide all of the benefits and features set forth herein, are also within the scope of this disclosure. Various structural, logical, and process step changes may be made without departing from the scope of the disclosure.

Throughout this application, the use of the singular form encompasses the plural form and vice versa. For example, "a", or "an" also includes a plurality of the referenced items, unless otherwise indicated.

Every numerical range given throughout this specification includes its upper and lower values, as well as every narrower numerical range that falls within it, as if such narrower numerical ranges were all expressly written herein, and every value is included to the tenth of the value of the lower limit.

The term "treatment" as used herein refers to alleviation of one or more symptoms or features associated with the presence of the particular condition or suspected condition being treated. Treatment does not necessarily mean complete cure or remission, nor does it preclude recurrence or relapses. Treatment can be effected over a short term, over a medium term, or can be a long-term treatment, such as, within the context of a maintenance therapy. Treatment can be continuous or intermittent.

The term "therapeutically effective amount" as used herein refers to an amount of an agent sufficient to achieve, in a single or multiple doses, the intended purpose of treatment. The exact amount desired or required will vary depending on the particular compound or composition used, its mode of administration, patient specifics and the like. Appropriate effective amount can be determined by one of ordinary skill in the art informed by the instant disclosure using only routine experimentation.

This disclosure provides modified lipopolysaccharide (LPS) molecules that act as vaccine adjuvants to enhance immune responses to an administered antigen. A modification comprises addition of phosphoethanolamine (PEtN) groups to the 1- and/or 4' phosphates on the lipid A or lipid A-based core (e.g., lipid $IV_A$ and de-O-acyl lipid A cores) of the molecule. The PEtN groups are linked to one or both phosphate(s) of the lipid A or lipid A-based molecules (e.g., lipid $IV_A$ and de-O-acyl lipid A molecules) via a phospho-anhydride bond. In an embodiment, the PEtN-modified saccharide(s) (e.g., PEtN-LPS molecules) of this disclosure retain TLR4 binding activity resulting in production of cytokines and an enhancement in immune responses. PEtN-modified saccharide (e.g., modified LPS molecules) of the present disclosure exhibit reduced toxicity.

This disclosure also provides modified lipid A and lipid A-based compounds (e.g., lipid $IV_A$ and de-O-acyl lipid A compounds) that act as vaccine adjuvants to enhance immune responses to an administered antigen. The lipid A and lipid A-based compounds (e.g., lipid $IV_A$ and de-O-acyl lipid A compounds) of this disclosure have reduced toxicity due to the addition of phosphoethanolamine (PEtN) groups to the 1- and/or 4' phosphates on the backbone of the molecules. The PEtN groups are linked to phosphates of the lipid A and lipid A-based compounds (e.g., lipid $IV_A$ and de-O-acyl lipid A compounds) via a phosphoanhydride bond. In an embodiment, the PEtN lipid A and lipid A-based compounds (e.g., lipid $IV_A$ and de-O-acyl lipid A compounds) of this disclosure retain TLR4 binding activity resulting in production of cytokines and an enhancement in immune responses.

Lipid A has the following structure:

Formula I

Lipid IV$_A$ has the following structure:

Formula II

De-O-acyl lipid A has the following structure:

Formula III

In an aspect, the present disclosure provides PEtN-modified saccharide(s) (e.g., compound) and PEtN-LPS molecules.

Figure 1:
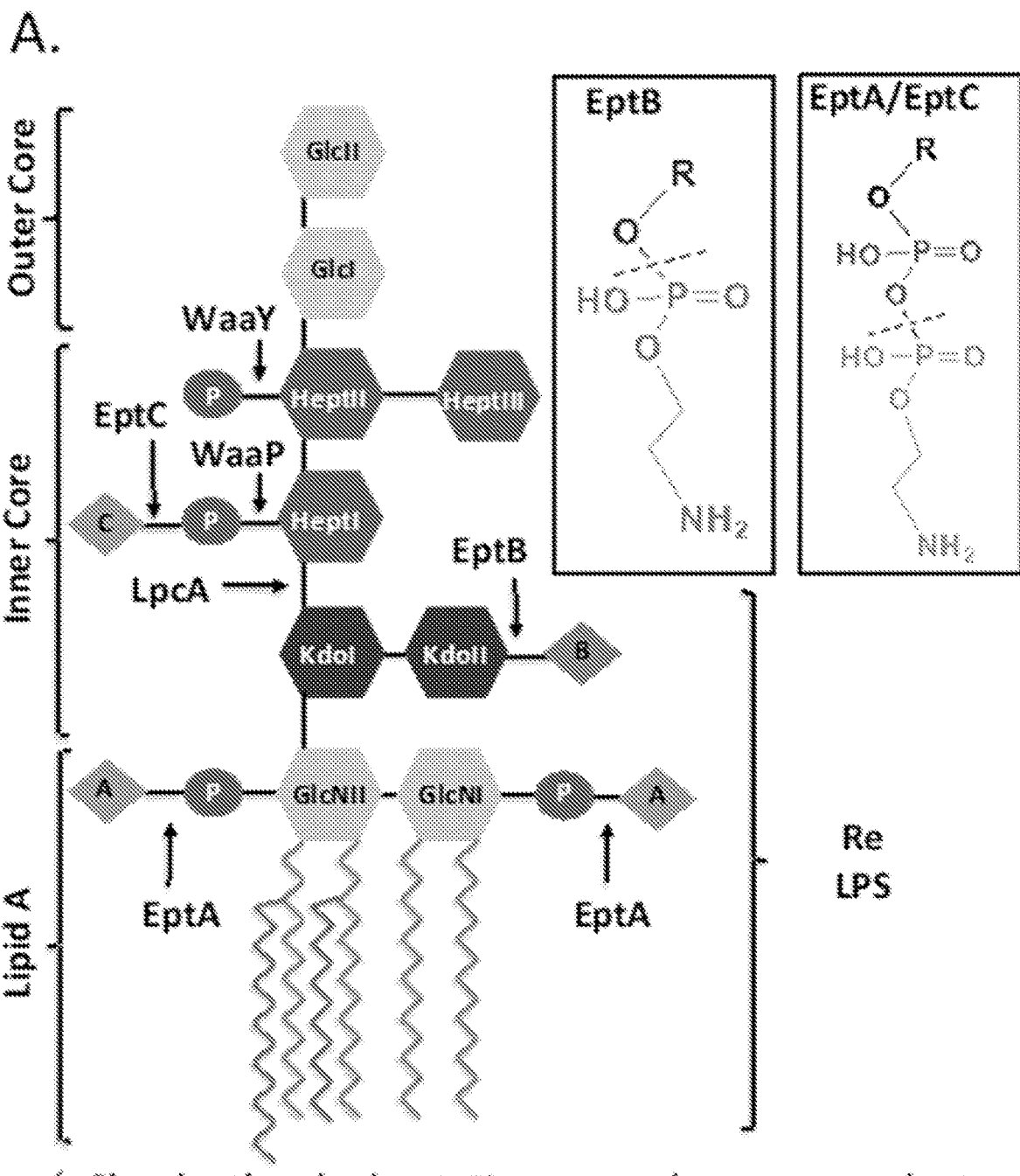
FIG. 1 shows inorganic phosphate released from LPS chemotypes in the presence of various alkaline phosphatases. (A) Schematic of hexa-acylated wildtype LPS chemotype from *E. coli* BL21 (DE3) with the nonstoichio-
metric phosphoanhydride (EptA/EptC) and phosphodiester
(EptB) linked PEtN modifications indicated. 4-Amino-4-
deoxy-L-arabinose (Ara4N) modifications (not shown)
share a common site of attachment with PEtN added by
EptA to lipid A substrate. The structure of Re LPS resulting
from lpcA deletion is indicated. LPS was extracted from
either wildtype (Wt) (B) or unmodified Re LPS (TXM333
ΔlpcAΔeptAΔarnA) (C) producing strains and incubated
with the indicated AP [100 μg/ml substrate, 50 mM Tris-HCl
(pH=8.25), 100 mM NaCl, 1 mM MgCl$_2$, 20 μM ZnCl$_2$ at
37° C.]. Phosphate release was measured using the mala-
chite green assay and the data plotted as the mean±the
standard deviation of three independent replicates.
Figure 1:
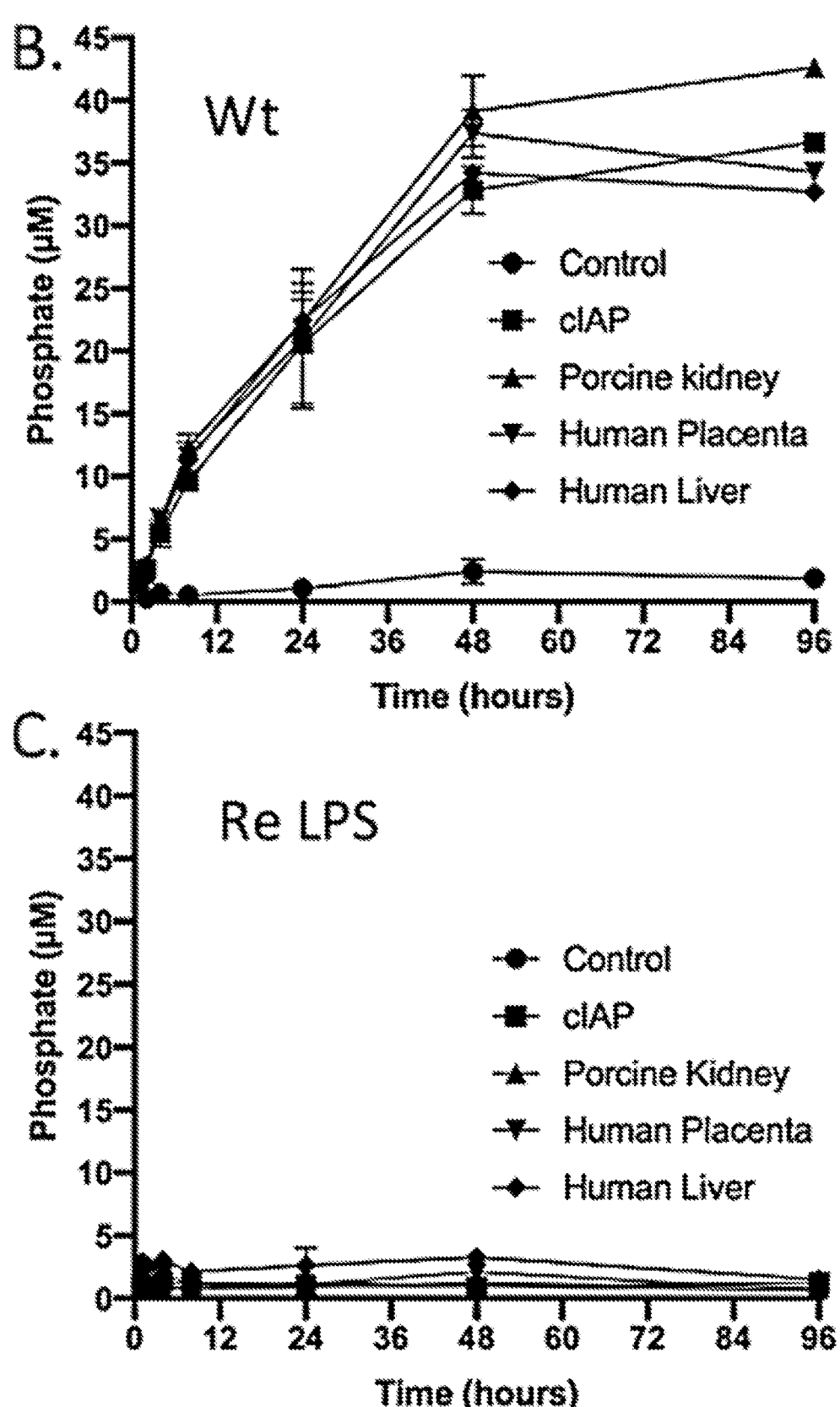

A PEtN-modified saccharide of the present disclosure may have the following structure:

Formula XXII where R$^1$ is H or an inner and outer core of LPS (as shown in FIG. 1);

$R^2$ is independently H or $R^5$ is H or an at least one $R^2$ is

The abbreviations in the FIG. 1 refer to the following: KdoI/KdoII—ketodeoxyoctulosonic acid; HepI/HepII/He-pIII—glycero-D-manno-heptulose; and GlcI/GlcII—D-glucose.

In an embodiment, a PEtN-modified saccharide is a PEtN-LPS molecule which comprises a lipid A core comprising one or two PEtN groups, a lipid $IV_A$ core comprising one or two PEtN groups, or a de-O-acyl lipid A core comprising one or two PEtN groups. A PEtN-LPS molecule may having the following structure:

$R^3$ is H,

, or

Formula IV

;

$R^4$ is H or

;

and

13
-continued

14
-continued

Formula V

Formula VII

Formula VI

Formula VIII

15

-continued

Formula IX

16

-continued

Formula XI

Formula X

Formula XII

In various embodiments, a PEtN-modified saccharide of the present disclosure is a PEtN-lipid A, PEtN-lipid IV$_A$, or PEtN-de-O-acyl lipid A compound. A PEtN-modified saccharide may have the following structure:

Formula XIII

Formula XIV

Formula XV

-continued

Formula XVI

Formula XVII

Formula XVIII

-continued

Formula XIX

Formula XX

Formula XXI

In one embodiment, this disclosure provides isolated PEtN-modified saccharide(s) (e.g., PEtN-LPS molecule(s) comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)). By the term "isolated" it is meant that the molecule is separated and/or recovered from its natural environment. The isolation of the PEtN-modified saccharide(s) from the natural environment can be such that the PEtN-modified saccharide(s) can be used without interference from other active agents (such as other proteins or lipids) that normally may be present in its natural environment.

In an example, the PEtN groups are attached to the 1- and/or 4' phosphates of the lipid A, lipid IVA, or de-O-acyl lipid A backbones of LPS by the enzyme EptA. EptA specifically recognizes lipid A. Additional details are provided herein.

LPS molecules and PEtN-modified saccharide (e.g., PEtN-LPS molecules) of the present disclosure may enhance an immune response to an antigen. The antigen may be a microbial antigen, such as a viral, fungal, parasitic, or bacterial antigen, or possibly a tumor antigen.

In an aspect, the present disclosure provides compositions. The compositions may comprise pharmaceutically acceptable carriers. The compositions may be immunogenic and/or vaccine compositions.

The immunogenic or vaccine compositions may comprise a pharmaceutically acceptable carrier or excipient, which typically does not produce an adverse, allergic or undesirable reaction when administered to an individual, such as a human subject, and one or more antigen(s). Pharmaceutically acceptable carrier or excipient may be fillers (solids, liquids, semi-solids), diluents, encapsulating materials and the like. Examples include, but are not limited to, saline, buffered saline, dextrose, water, glycerol, ethanol, and the like, and combinations thereof. The compositions may also contain wetting or emulsifying agents, biological buffers, and the like, and combinations thereof. A biological buffer is any solution that is pharmacologically acceptable and provides a formulation (e.g., adjuvant formulation) with the desired pH (e.g., a pH in the physiological range). Examples of buffer solutions include saline, phosphate buffered saline, Tris buffered saline (TBS), Hank's buffered saline (HBS), growth media such as Eagle's Minimum Essential Medium ("MEM"), and the like.

Compositions of the present disclosure may suitable for administration to a subject may be prepared by mixing PEtN-modified saccharide(s) (e.g., isolated PEtN-modified saccharide(s) (e.g., the isolated PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)) and/or the antigen with any suitable pharmaceutically acceptable carriers, excipients and/or stabilizers. Some examples of compositions suitable for mixing with the agent can be found in Remington: The Science and Practice of Pharmacy (2005) 21st Edition, Philadelphia, PA Lippincott Williams & Wilkins.

Without intending to be bound by any particular theory, it is considered that the present compounds and compositions may be used to enhance an immune response to any antigen. The antigens may include, but are not limited to, protein antigens, polypeptide or peptide antigens. An antigen may be well characterized, or may be unknown, other than by a known presence in, for example, a lysate from a particular cell type.

In various embodiments, an antigen that facilitates an enhanced immune response is a viral antigen. Viral antigens may be obtained by conventional techniques, such as, for example, by preparation of viral or cell lysates generated in vitro by tissue culture. The antigen can be used in a purified form or in partially purified or unpurified form as a crude viral or cell lysate. Alternatively, the antigen may be expressed by recombinant DNA techniques in any of a wide variety of expression systems. Thus, it will be recognized that PEtN-modified saccharide(s) (e.g., isolated PEtN-modified saccharide(s) (e.g., isolated PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules))) may be provided for use such that discreet, PEtN-modified saccharide(s) (e.g., isolated PEtN-modified saccharide(s) (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules))) are complexed with different antigens. Such complexes can be formed using various conditions, such as differing PEtN-modified saccharide(s) (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules))) to antigen ratios, a variety of buffers, incubation times, and temperatures.

In various embodiments, the antigens may be expressed by infections agents. Examples of such infectious agents include, but are not limited to, viruses, bacteria, fungi, and other parasites. Examples of viruses include, but are not limited to, human papilloma virus, hepatitis type B or type C, influenza, varicella, adenovirus, herpes simplex virus type I or type II, rinderpest, rhinovirus, echovirus, rotavirus, respiratory syncytial virus, papova virus, cytomegalovirus, echinovirus, arbovirus, hantavirus, coxsachie virus, mumps virus, measles virus, rubella virus, polio virus, and human immunodeficiency virus type I or type II. Examples of bacteria include, but are not limited to, *M. tuberculosis, Mycobacterium, Mycoplasma, Neisseria* and *Legionella*. Examples of other parasites include, but are not limited to, *Rickettsia* and *Chlamydia*. In an example, composition may comprise an antigen to stimulate an anti-viral immune response from human papilloma virus.

In various embodiments, an antigen of the present disclosure that facilitates an enhanced immune response is a tumor antigen. Tumor antigens may be obtained by conventional techniques, such as by preparation of tumor cell lysates by repeatedly freezing and thawing tumor cells/ tissues obtained from fresh tumor biopsy tissues or from tumor cells generated in vitro by tissue culture. The tumor lysate may be obtained by centrifugation and harvesting the supernatant fluid. The tumor cell lysates may be used immediately or frozen and stored until ready for use. The antigen may be used in a purified form or in partially purified or unpurified form as cell lysate. Alternatively, the antigen may be expressed by recombinant DNA techniques in any of a wide variety of expression systems. Thus, it will be recognized that PEtN-modified saccharide(s) (e.g., isolated PEtN-modified saccharide(s) (e.g., isolated PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules))) may be provided for use such that discreet, PEtN-modified saccharide(s) (e.g., isolated PEtN-modified saccharide(s) (e.g., isolated PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules))) are complexed with different antigens. Such complexes may be formed using various conditions, such as a differing PEtN-modified saccharide (e.g., a differing PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules))) to antigen ratios, a variety of buffers, incubation times, and temperatures.

In various embodiments, the antigen may be an antigen expressed by any type of cancer cell, specific examples of which include but are not limited to fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, Waldenstrom's macroglobulinemia, and heavy chain disease.

As an illustrative example, the present disclosure provides PEtN-modified saccharide(s) (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)), which can be isolated molecules, which specifically bind to TLR4, which can be human TLR4. As an example, molecules designated PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules) are provided. Specifically, these molecules bind to TLR4. TLR4 is a member of the Toll-like receptor (TLR) family. Interaction of TLRs with their ligands initiates the release of inflammatory mediators such as pro-inflammatory cytokines and the maturation/activation of cells involved in an immune response. Both inflammation and immune cell maturation/activation are required for induction of antigen-specific immunity, including anti-viral and anti-tumor immunity. Agents capable of triggering inflammation and immune cell maturation/activation may be referred to as adjuvants. Adjuvants can enhance cellular and humoral (antibody) immune responses.

Without intending to be bound by any particular theory, it is considered that PEtN-modified saccharide(s) (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)) enhance cytokine production. PEtN-modified saccharide(s) (e.g., PEtN-LPS) comprising a lipid A or a lipid A-based core (e.g., lipid $IV_A$ and de-O-acyl lipid A core) and PEtN-lipid A and lipid A-based molecules (e.g., lipid $IV_A$ and de-O-acyl lipid A molecules) interact with TLR4 on the surface of somatic cells and immune cells responsible for induction of antigen specific immunity (such as dendritic cells and macrophages). PEtN-modified saccharide) (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)) interaction with TLR4 leads to the activation of NF-kB and maturation/activation of dendritic cells and macrophages and secretion of pro-inflammatory cytokines. Thus, PEtN-modified saccharide(s) (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)) are immune adjuvants and may be included in vaccine formulations.

A composition of the present disclosure may further comprise an adjuvant. An adjuvant may be used with the administration of vaccines (e.g., a composition of the present disclosure). For example, an adjuvant may have a concentration of 0.001 to 50 wt % in solution (e.g., in a phosphate buffered saline solution) including all 0.0001 wt % values and ranges therebetween, and the antigen may be present on the order of micrograms to milligrams, such as about 0.0001 to about 5 wt %, such as about 0.0001 to about 1 wt %, such as about 0.0001 to about 0.05 wt %. The antigen may be present in an amount on the order of micrograms to milligrams, or, about 0.001 to about 20 wt %, such as about 0.01 to about 10 wt %, or about 0.05 to about 5 wt %.

An adjuvant may be a part of a vaccine composition for introduction into a human or animal to be vaccinated. Immunogenic compositions may be formulated for administration via systemic, dermal, or mucosal routes. These include, but are not limited to, subcutaneous, transdermal, intradermal, intramuscular, intraperitoneal, intravenous, ocular, intranasal, oral, and by inhalation. The vaccine may further comprise a physiological carrier such as a polymer.

In one embodiment, the vaccine is formulated for intramuscular administration. In other embodiments, the vaccine is formulated for intradermal, intraperitoneal, intravenous, subcutaneous, ocular, intranasal, mucosal, sublingual, buccal or oral administration. In an embodiment, the vaccine is formulated as an intramuscular vaccine. Routes and frequency of administration of the therapeutic compositions disclosed herein, as well as dosage, will vary from individual to individual, and may be readily established using standard techniques.

In an embodiment, the PEtN-modified saccharide(s) (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)) and an antigen are present in a composition of the present disclosure as a complex, and may be covalently or non-covalently associated. For example, the PEtN-modified saccharide(s) (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)) and the antigen may be joined to each other by chemical bonding, such as by covalent bonds, ionic bonds, hydrogen bonds, and/or van der Waals forces, or combinations thereof. Methods for forming adjuvant/antigen complexes with or without covalent bonding are known in the art and may be employed to form complexes between isolated PEtN-modified saccharide(s) (e.g., isolated PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules) and one or more antigens. Complexes of the present disclosure may comprise PEtN-modified saccharide(s) (e.g., an isolated PEtN-modified saccharide (e.g., isolated PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules))) and an antigen, or may consist essentially of a PEtN-modified saccharide (e.g., an isolated PEtN-modified saccharide (e.g., isolated PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules))) and an antigen, or may consist of a PEtN-modified saccharide (e.g., an isolated PEtN-modified saccharide (e.g., isolated PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules))) and an antigen. An isolated molecule does not necessarily have to be a purified molecule. However, isolated PEtN-modified saccharide(s) (e.g., isolated PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)) may nevertheless be purified to any desired degree of purification for use in the present disclosure. Isolated PEtN-modified saccharide(s) (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)) include PEtN-modified saccharide(s) (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)) produced by recombinant methods.

In an aspect, the present disclosure provides methods of using compounds and compositions of the present disclosure. The methods may be used to generate and/or enhance an immune response in an individual.

A method of the present disclosure may comprise administering to an individual (e.g., an individual in need of treatment) an effective amount of one or more PEtN-modified saccharide(s) or a composition comprising one or more PEtN-modified saccharide(s) of the present disclosure.

In various examples, the administered composition may further comprise one or more antigens against which an immune response is desired. In various examples, the PEtN-modified saccharide(s) and antigen(s) are administered simultaneously. In various other examples, the PEtN-modified saccharide(s) and antigen(s) are administered at different times (e.g., in different compositions).

Administration of compounds or compositions may be performed in conjunction with conventional therapies that are intended to treat a disease or disorder associated with an antigen. For example, a composition could be administered prior to, concurrently, or subsequent to conventional anticancer therapies. Such therapies can include but are not limited to, chemotherapies, surgical interventions, and radiation therapy.

In general, a desirable dosage and treatment regimen provides the composition in an amount effective to stimulate an immune response that provides a therapeutic and/or prophylactic benefit. Such a response can be monitored by an improved clinical outcome, e.g., inhibition in tumor growth and/or metastasis, improved resistance to infection, improved immune cell activation, and/or other parameters that will be apparent to those skilled in the art, dependent upon the condition being treated.

In an embodiment, a PEtN-modified saccharide (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules))/antigen complex can be used to prime antigen presenting cells (APCs), such as, for example, dendritic cells, and primed APCs can be administered to an individual to achieve an enhanced immune response against the individual. Thus, in an embodiment, the present disclosure provides compositions comprising an isolated population of APCs and a complex comprising isolated PEtN-modified saccharide(s) (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)) and an antigen.

The present disclosure provides methods for enhancing an immune response to an antigen in an individual comprising administering to the individual an effective amount of (a) PEtN-LPS comprising a lipid A or a lipid A-based core (e.g., lipid $IV_A$ and de-O-acyl lipid A core) or (b) PEtN-lipid A or PEtN-lipid A-based molecules (e.g., lipid $IV_A$ and de-O-acyl lipid A molecules), and (c) an antigen, whereby the PEtN-modified saccharide(s) (e.g., PEtN-LPS comprising a lipid A or a lipid A-based core (e.g., lipid $IV_A$ and de-O-acyl lipid A core) and/or PEtN-lipid A or PEtN-lipid A-based molecules (e.g., lipid $IV_A$ and de-O-acyl lipid A molecules)) act as an adjuvant to enhance the immune response to the antigen.

In an embodiment, an adjuvant is a toxin such as endotoxin or a modified form of endotoxin. In some embodiments, the adjuvant is PEtN-LPS or a subunit or derivative thereof, such as PEtN-lipid $IV_A$, which is effective in generating an immune response against an antigen. For example, the antigen may be selected from a group of antigens from human papilloma virus such as, for example, L1, E6, or E7.

In an aspect, this disclosure provides a kit comprising an administration device suitable for administration and an immunogenic formulation comprising an adjuvant and an antigen as described herein. In another aspect, this disclosure provides a kit comprising separate formulations of the adjuvant and the antigen. These separate formulations may be mixed together and administered to an individual or they may be administered separately. The device may be supplied pre-filled with the immunogenic formulation. In one embodiment, the immunogenic formulation is in a liquid volume smaller than for conventional intramuscular vaccines. For example, the intramuscular administration devices may contain a volume of between about 0.05 ml and 5.0 ml. The kit may also contain a needle delivery device suitable for the appropriate administration route.

The following Statements provide examples of the present disclosure:

Statement 1. A PEtN-modified saccharide having the following structure:

Formula XXII where $R^1$ is H or the inner and outer core of LPS; $R^2$ is independently $R^3$ is H, , or

;

$R^4$ is H or

;

and $R^5$ is H or

.

Statement 2. A PEtN-modified saccharide (e.g., modified lipopolysaccharide (LPS) molecule) having a lipid A backbone, a lipid $IV_A$ backbone, or a de-O-acyl lipid A backbone comprising a phosphoethanolamine group at position C1 and/or a phosphoethanolamine group at position C4' of the lipid A backbone, the lipid $IV_A$ backbone, or the de-O-acyl lipid A backbone having the following structure:

Formula IV 31    32

-continued

Formula V

Formula VI

Formula VII 33                                                                                      34

-continued

Formula VIII                                                          Formula IX Formula X -continued Formula XI Formula XII Statement 3. A PEtN-modified saccharide (e.g., modified lipid A molecule) comprising a phosphoethanolamine group at position C1 and/or a phosphoethanolamine group at position C4' of the lipid A molecule having the following structure:

Formula XIII

-continued

Formula XIV

Formula XV

Statement 4. A PEtN-modified saccharide (e.g., modified lipid $IV_A$ molecule) comprising a phosphoethanolamine group at position C1 and/or a phosphoethanolamine group at position C4' of the lipid $IV_A$ molecule having the following structure:

Formula XVI

-continued

Formula XVII                                                                      Formula XVIII Statement 5. A PEtN-modified saccharide (e.g., modified
de-O-acyl lipid A molecule) comprising a phosphoetha-
nolamine group at position C1 and/or a phosphoetha-
nolamine group at position C4' of the de-O-acyl lipid A
molecule having the following structure:

Formula XIX

-continued

Formula XX

Formula XXI

Statement 6. A composition comprising a PEtN-modified saccharide according to any one of the preceding Statements. The composition may further comprise a pharmaceutically acceptable carrier.

Statement 7. A vaccine composition comprising a PEtN-modified saccharide according to any one of the preceding Statements, an antigen, and a suitable pharmaceutically acceptable carrier.

Statement 8. A method for generating an immune response in an individual comprising administering to an individual in need of treatment an effective amount of a composition according to Statements 6 or 7.

Statement 9. A method of enhancing an immune response in an individual comprising administering to an individual an effective amount of a PEtN-modified saccharide according to Statements 1-5, wherein the PEtN-modified saccharide is administered in conjunction (e.g., at the same time or at different times or in the same composition or in a different composition) with an antigen against which an immune response is desired.

Statement 10. A method according to Statement 9, where the PEtN-modified saccharide according to any one of Statements 1-5 and the antigen are administered at the same time (e.g., in the same composition).

Statement 11. A method according to Statement 9, where the molecule according to any one of Statements 1-5 and the antigen are administered at different times (e.g., in different compositions).

Statement 12. A method according to any one of Statements 8-11, where the antigen is a peptide or protein.

Statement 13. A method according to any one of Statement 1-5, where the PEtN-modified saccharide binds to TLR4.

The following example is presented to illustrate the present disclosure. It is not intended to be limiting in any matter.

EXAMPLE

This example describes the synthesis and TLR4 agonist activity of PEtN-LPS comprising a lipid A or a lipid A-based core (e.g., lipid $IV_A$ and de-O-acyl lipid A core) and PEtN-lipid A and lipid A-based molecules (e.g., lipid $IV_A$ and de-O-acyl lipid A molecules).

Results

Inorganic Phosphate is Only Released from Wildtype *E. coli* B LPS Chemotype.

To study the impact of LPS modifications on processing by AP, a highly purified *E. coli* B LPS feedstock sample was first isolated using an extended protocol that included specific steps to remove phospholipid and nucleic acids contaminants that could contribute to background phosphate release. *E. coli* B was chosen as the parent LPS strain source firstly because of a native insertion sequence element within the outer saccharide core waaT gene, encoding for a UDP-galactose: (glucosyl) LPS α1,2-galactosyltransferase glycosyltransferase, that truncates the LPS to a structure of relatively low complexity, and secondly for the high levels of endogenous PEtN and Ara4N modifications observed when this strain is grown in standard rich medium (FIG. 1A). Analysis by mass spectrometry confirmed a highly PEtN/Ara4N-substituted LPS (FIG. 9A), with an average total phosphate content of between 4 to 5 Pi equivalents per molecule of LPS (Table 1). Calf intestinal alkaline phosphatase (cIAP) was initially tested with LPS preparations from wildtype *E. coli* B LPS for phosphate release using the inorganic phosphate specific malachite green assay (FIG. 1B). While phosphate release was readily detected, the amount plateaued well short of the total LPS-associated phosphate input (~25 μM LPS with 100-125 μM total phosphate). Since there are multiple tissue specific AP isoforms, a panel of commercially available APs was tested to determine if a more robust phosphate release could be realized. However, all APs demonstrated a plateau similar to cIAP even after a prolonged 96-hour incubation period (FIG. 1B). Varying reaction conditions by adding bile salts to act as detergent, bovine serum albumin, 10% whole serum, or extensive pre-sonication of LPS vesicles did not appreciably enhance the amount of phosphate released (data not shown). Detection of inorganic phosphate was completely dependent on inclusion of AP. This suggested that only a fraction of the total LPS phosphate content was subject to hydrolysis, irrespective of either the AP isoform or presence of de-aggregation agents.

To determine which LPS phosphate group(s) was being released, the assay was repeated using a structurally defined Re LPS chemotype as substrate. Re LPS extracted from *E. coli* TXM333 lacks all sugars but Kdo (3-deoxy-α-d-manno-oct-2-ulosonic acid) from the saccharide core due to deletion of the d-sedoheptulose 7-phosphate isomerase gene lpcA (gmhA) as well as all types of PEtN/Ara4N modifications on lipid A due to deletions in the respective biosynthetic genes eptA/arnA (FIG. 1A). Re LPS was extensively purified as described above for wildtype, and analysis by MS confirmed a nearly homogeneous population of the Re chemotype (FIG. 9B and Table 1). In contrast to assays with wild type LPS, no phosphate was liberated from Re chemotype when incubated under identical conditions (FIG. 1C). This indicated that the core lipid A phosphates are not efficiently cleaved by APs, and that the phosphate liberated from wildtype LPS must originate from either lipid A PEtN or saccharide core modifications attached distal to Kdo residues.

produced by strains harboring various combinations of eptA/B/C (FIG. 2B) was thus tested. All strains were ΔarnA to limit any variability arising from substrate competition by Ara4N with eptA. Since the native promoters of each of the PEtN transferases is subject to complex regulation, constructs with constitutive promoters were used to achieve comparable high-level PEtN modification levels as assessed by MS (FIG. 10). Next to ΔeptA, the least amount of phosphate release was detected from LPS extracted from strains lacking EptC and WaaP, the HepI kinase that forms the P-HepI acceptor substrate utilized by EptC. Overexpression of EptC, but not EptB, enhanced phosphate release although the amount remained well below EptA. The data collectively suggests EptA installs most of the total labile phosphate pool in *E. coli* wild type LPS, with EptC making a minor contribution. The phosphate content added by EptB is stable to hydrolysis.

PEtN Release from LPS is Spontaneous.

The PEtN groups attached by EptA and EptC are both connected by a phosphoanhydride bond, while EptB installs a typical phosphodiester bond at KdoII (FIG. 1A, inset). The data thus supported one of three scenarios, wherein either: i.)

TABLE 1

MS peak list of major glycoforms detected in wildtype *E. coli* BL21
(DE3) and TXM333 (ΔlpcAΔeptAΔarnA) expressing unmodified Re LPS[a]

| Obs. Mass [u] | Calc. Mass [u] | Chemical Composition[a] | | | | | | |
|---|---|---|---|---|---|---|---|---|
| Wildtype | | | | | | | | |
| 3420.63 | 3420.6096 | LA$_{hexa}$[b] | 2* Kdo | 3* Hep | 2* Hex | 2* P | 1* P-EtN | |
| 3543.62 | 3543.6181 | LA$_{hexa}$ | 2* Kdo | 3* Hep | 2* Hex | 2* P | 2* P-EtN | |
| 3551.66 | 3551.6676 | LA$_{hexa}$ | 2* Kdo | 3* Hep | 2* Hex | 2* P | 1* P-EtN | 1* Ara4N |
| *3666.61* | *3666.6266* | *LA$_{hexa}$* | *2* Kdo* | *3* Hep* | *2* Hex* | *2* P* | *3* P-EtN* | |
| *3674.65* | *3674.6761* | *LA$_{hexa}$* | *2* Kdo* | *3* Hep* | *2* Hex* | *2* P* | *2* P-EtN* | *1* Ara4N* |
| 3789.65 | 3789.6351 | LA$_{hexa}$ | 2* Kdo | 3* Hep | 2* Hex | 2* P | 4* P-EtN | |
| 3797.68 | 3797.6846 | LA$_{hexa}$ | 2* Kdo | 3* Hep | 2* Hex | 2* P | 3* P-EtN | 1* Ara4N |
| Re LPS | | | | | | | | |
| 1800.96 | 1800.9443 | LA$_{tetra}$[c] | 2* Kdo | | | | | |
| 2027.14 | 2027.1376 | LA$_{penta}$[d] | 2* Kdo | | | | | |
| 2237.41 | 2237.3360 | LA$_{hexa}$ | 2* Kdo | | | | | |

[a]Italicized entries are most abundant peaks in wildtype MS spectrum (FIG. 9A).
[b]LA$_{hexa}$: 2*14:0(3-OH), 1*14:0[3-O(12:0)], 1*14:0[3-O(14:0)]
[c]LA$_{tetra}$: 2*14:0(3-OH), 1*14:0[3-O(12:0)]
[d]LA$_{penta}$: 3*14:0(3-OH), 1*14:0[3-O(12:0)]

Released Phosphate Originates from PEtN Added by EptA and EptC

Figure 2:
FIG. 2 shows phosphate released during incubation of (A)
BL21 (DE3) (wt), TXM322 (ΔarnA), GKM329 (ΔeptA),
TXM331 (ΔeptAΔarnA), TXM333 (Re LPS,
ΔlpcAΔeptAΔarnA), TXM343 (Re LPS,
ΔlpcAΔeptAΔarnA+pEptA), and (B) TXM331
(ΔeptAΔarnA), GKM373 (ΔeptAΔarnAΔeptB), GKM374
(ΔeptAΔarnAΔeptC), GKM357 (ΔeptAΔarnAΔwaaP),
GKM380 (ΔeptAΔarnAΔeptB+pEptC), GKM381
(ΔeptAΔarnAΔeptC+pEptB), TXM402
(ΔeptAΔarnAΔeptC+pEptA), and GKM358
(ΔeptAΔarnAΔwaaP+EptA) with cIAP [100 μg/ml sub-
strate, 4 U/ml, 50 mM Tris-HCl (pH=8.25), 100 mM NaCl,
1 mM MgCl$_2$, 20 μM ZnCl$_2$ at 37° C.]. Released phosphate
was measured after 48 hours of incubation using the mala-
chite green assay and normalized to BL21 (DE3) (wt). Data
are representative of three independent experiments con-
ducted in duplicates and the error bars show SDs. +/−
indicates chromosomal genes, (P) denotes gene introduced
on a plasmid.
Figure 2:
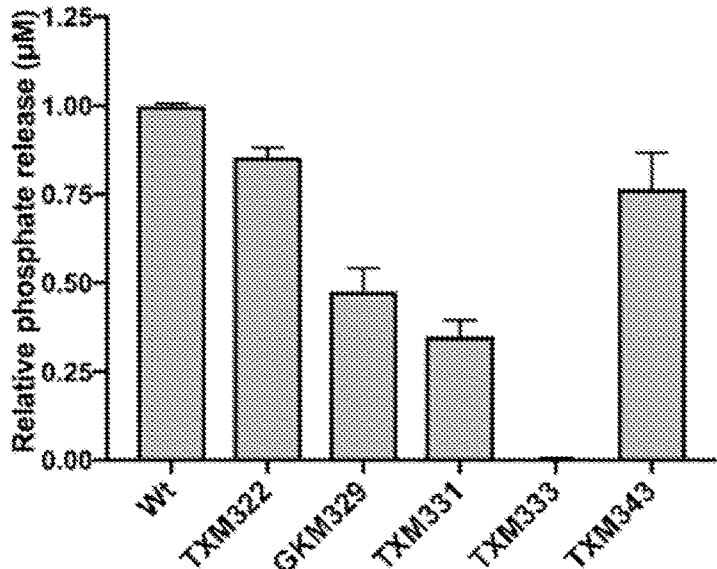
Figure 2:
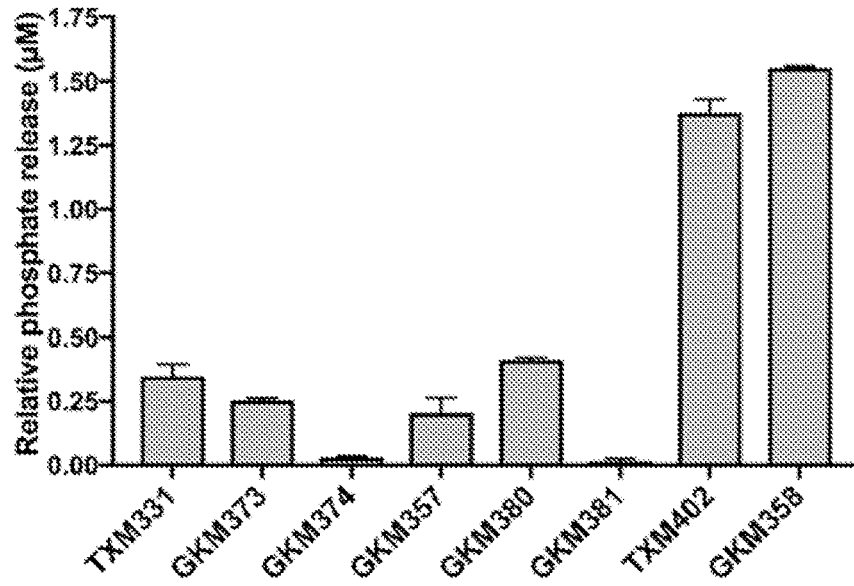

PEtN groups are added in nonstoichiometric amounts to LPS at three distinct positions by a set of related membrane-bound transferases: i.) EptA onto either lipid A phosphate, ii.) EptB onto KdoII, or iii.) EptC onto phosphorylated HepI (1-glycero-d-manno-heptose). A a panel of deletions in eptA was first constructed, since this transferase can add PEtN to both phosphates of lipid A (FIG. 1A). Indeed, the amount of phosphate released was closely correlated with the presence of EptA, and plasmid-borne EptA alone restored phosphate release when testing Re LPS chemotype as substrate (FIG. 2A). Deletion of arnA, which modifies lipid A phosphate groups with Ara4N, alone or in tandem with eptA had minimal impact on phosphate release.

Figure 3:
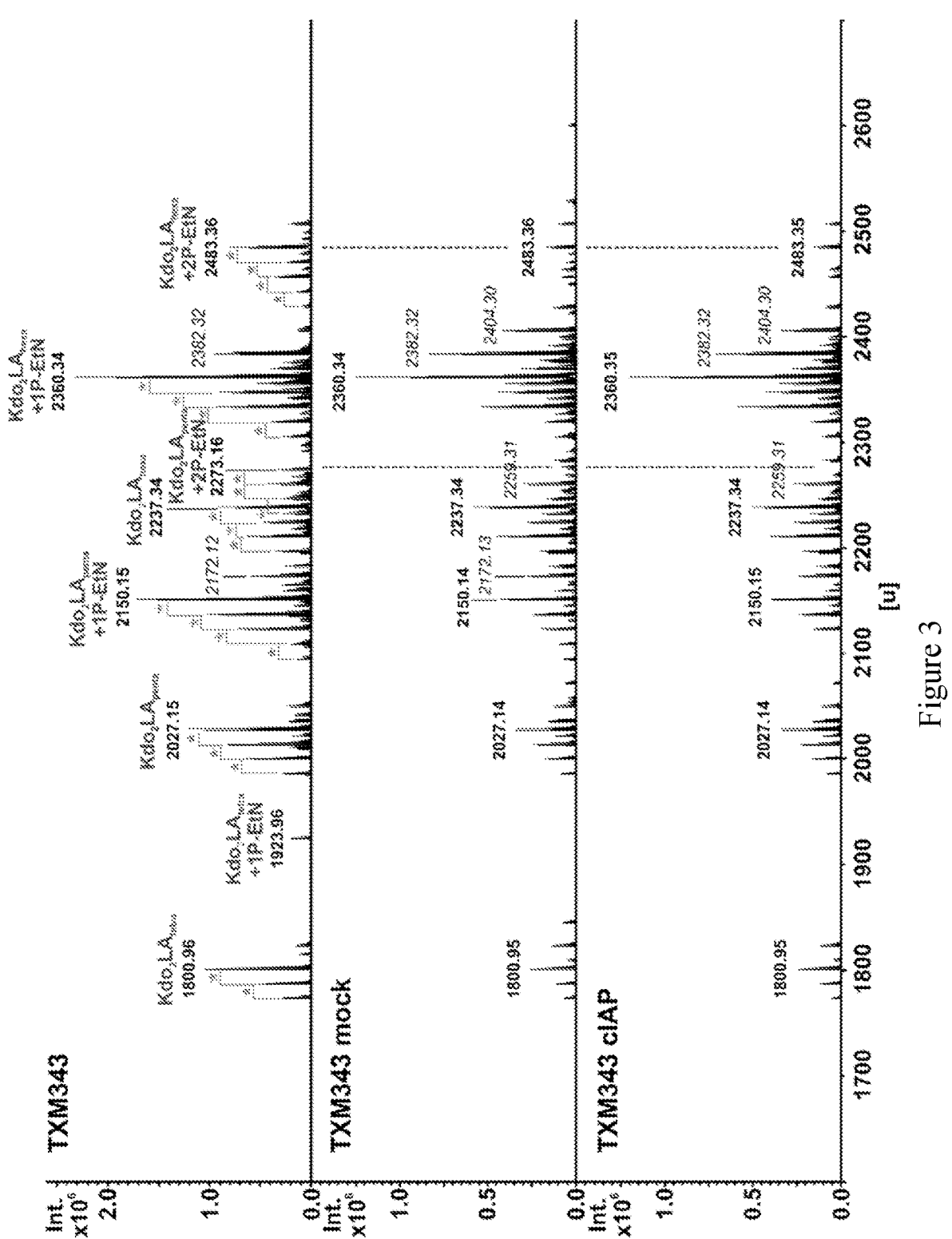
FIG. 3 shows MS analysis of EptA-modified Re LPS. Re
LPS was extracted from TXM343 [lpcA::gentR eptA::catR
arnA::kanR (pSEVA434-eptA)] and analyzed by MS.
Samples were either directly analyzed (top panel), or incu-
bated for 16 hours at 37° C. in buffer [100 μg/ml substrate,
50 mM Tris-HCl (pH=7.1), 100 mM NaCl, 1 mM MgCl$_2$, 20
μM ZnCl$_2$] alone (mock) or with cIAP (4 U/ml). Masses in
italic type represent sodium adducts (Δm=22 u), while those
marked with a green star account for a difference of Δm=14
u, consistent with a methylene unit (—CH$_2$—). Chemical
composition assignments (red) for unmodified Re LPS spe-
cies are listed in Table 1.

While phosphate installed by EptA accounted for the bulk of the total released, significant amounts of phosphate (up to ~30% of the total) were still liberated from LPS chemotypes isolated from ΔeptA strain backgrounds. This suggests some of the detected phosphate originated from the saccharide core as well. Phosphate liberation from LPS chemotypes cIAP specifically recognizes PEtN residues attached by EptA/EptC, ii.) cIAP only cleaves phosphoanhydride linked PEtN groups, or iii.) PEtN connected through a phospho-anhydride bond spontaneously hydrolyzes to free O-PEtN monoester that then becomes the actual substrate for cIAP. It was initially suspected the third scenario, given the known instability of high-energy phosphoanhydride bonds and because the majority of characterized AP substrates are phosphomonoesters. To test for non-enzymatic hydrolysis, Re LPS modified with phosphoanhydride linked PEtN added by EptA (from TXM343) was incubated with or without cIAP, extracted, and analyzed by MS for doubly modified, singly modified, and unmodified Re LPS (FIG. 3). PEtN hydrolysis was monitored by a mass shift of Δm=123 u, which corresponds to a single PEtN residue. While the total PEtN content clearly decreased after incubation (buffer pH=7.1, 16 hours) when compared to directly injected samples, the MS profile of mock-treated Re LPS was nearly indistinguishable from cIAP-treated samples (FIG. 3, middle and bottom panels).

Figure 4:
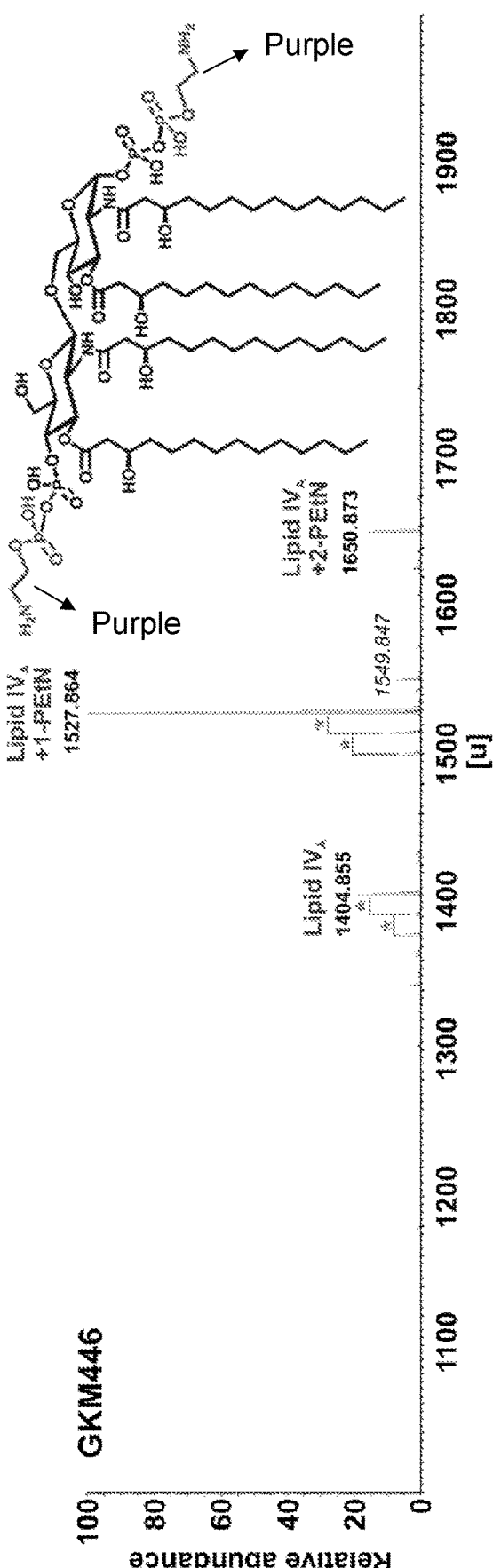
FIG. 4 shows hydrolysis of phosphoanhydride linked
PEtN-lipid IV$_A$ is spontaneous and pH dependent. (A) MS
analysis in the negative anion mode of lipid IV$_A$ isolated
from GKM446
(ΔeptAΔgutQΔkdsDΔlpxLΔlpxMΔlpxPΔpagP+pEptA).
The structure of lipid IV$_A$ modified with two PEtN residues
in non-stoichiometric amounts at C1-GlcNI and C4'-GlcNII
when EptA is expressed is indicated (purple). Masses in
italic style represent sodium adducts (Δm=22 u), differences
marked with a star account for a difference of Δm=14 u,
consistent with a methylene unit (—CH$_2$—). (B) Phosphate
release was measured as a function of increasing concen-
trations of cIAP after incubation for 6 hours at 37° C. [100
μg/ml PEtN-lipid IV$_A$ substrate, 50 mM Tris-HCl
(pH=8.25), 100 mM NaCl, 1 mM MgCl$_2$, 20 μM ZnCl$_2$]
using PEtN-lipid IV$_A$ substrate isolated from GKM446.
Phosphate was measured using the malachite green assay,
and data are representative of two independent experiments
conducted in triplicate with the error bars showing SDs. (C)
Either lipid IV$_A$ alone (ClearColi® K-12 GKM445
ΔeptAΔgutQΔkdsDΔlpxLΔlpxMΔlpxPΔpagP) or with PEtN
added by EptA (GKM446
Figure 4:
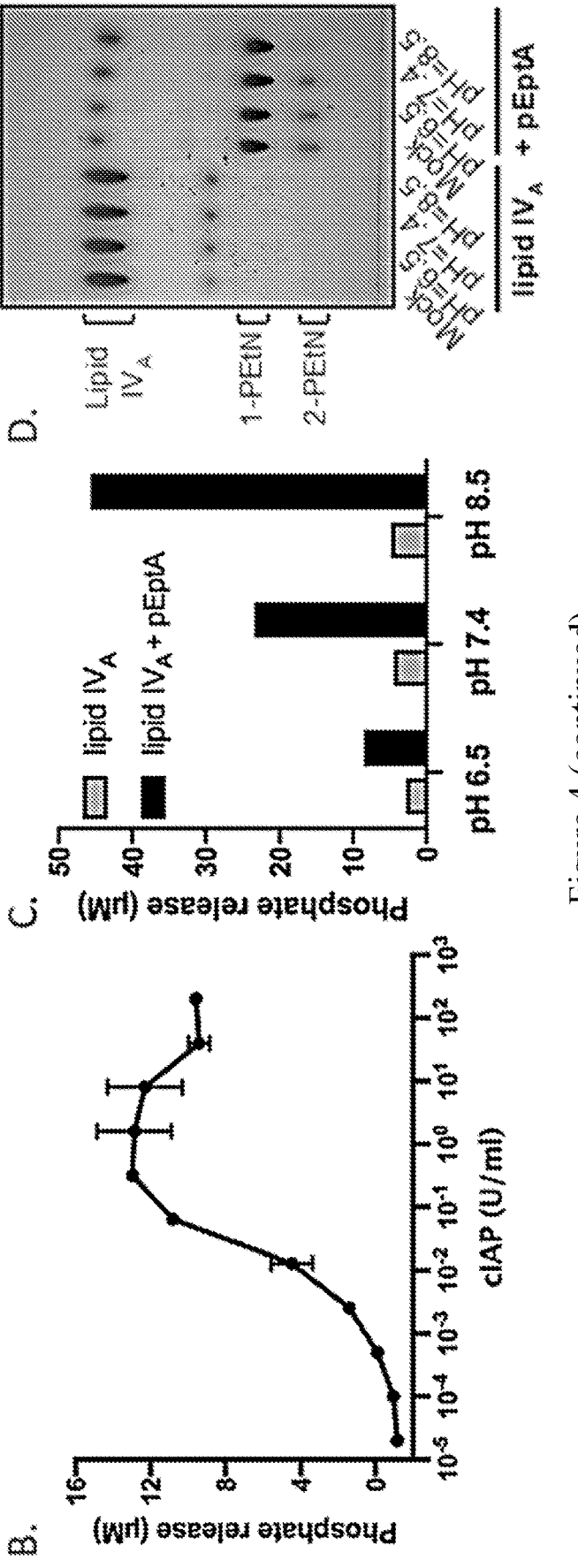

To confirm spontaneous (i.e. non-enzymatic) hydrolysis, a second set of PEtN-modified chemotypes with a more homogenous composition was examined since quantitative comparison of Re LPS MS peaks is complicated by multiple glycoforms within the same population. Previously a mutant *E. coli* strain was constructed that elaborates only lipid $IV_A$, a chemotype lacking glycosylation with uniform 3-O—C14:0 tetra-acylation, that remains viable due to suppressor mutations in LPS transport systems. By introducing pEptA into this genetic background, PEtN-modified lipid $IV_A$ substrate preparations with 2-PEtN, 1-PEtN, or unmodified lipid $IV_A$ (FIG. 4A) were obtained. When assayed for phosphate release, a nonlinear correlation between the amount of released inorganic phosphate and the units of cIAP added was observed well before the total amount of input PEtN-linked lipid $IV_A$ phosphate should become rate limiting (FIG. 4B). This is consistent with an initial slower, non-enzymatic hydrolytic step preceding cIAP catalysis, namely the putative dephosphorylation of free PEtN. To support this theory, the O-PEtN monoester was directly tested as a substrate for cIAP and typical Michaelis-Menten kinetics ($K_m$ of 173±27 μM for O-PEtN and $V_{max}$ of 1.09±0.05 μM/min) were observed (FIG. 11A). Using the crystal structure of the highly homologous rat IAP ortholog (~70% identity with cIAP across 486 non-gapped residues) as a model, O-PEtN can be readily accommodated within the substrate binding pocket in the active site (FIG. 11B). This is in contrast to modeling of acylated lipid A as the putative IAP substrate (see below).

Hydrolysis of Phosphoanhydride-Linked PEtN from LPS is pH Dependent.

The stability of PEtN linkages attached by EptA on lipid $IV_A$ was tested by incubation in buffer at defined pH (FIG. 4C). Liberated PEtN was indirectly quantified by adding excess cIAP at the end of the incubation period and measuring inorganic phosphate levels using the malachite green assay. The extent of phosphate released increased as the pH of the pre-incubation buffer was raised, consistent with a base-labile phosphoanhydride bond. Hydrolysis was minimal at acidic pH. A mildly acidic environment naturally induces eptA expression and lipid A modification with PEtN in *E. coli* and *Salmonella enterica*. The incubation was repeated a second time, except the resulting lipid $IV_A$ population was extracted and separated by TLC before being visualized by sulfuric acid charring (FIG. 4D). Unmodified lipid $IV_A$ was stable across the entire pH range tested, whereas the dually modified 2-PEtN lipid $IV_A$ population disappeared with a concomitant increase in free lipid $IV_A$ as hydrolysis incubation conditions became more basic. Considering no cIAP was utilized, this data in combination with the qualitative MS results using PEtN-modified Re LPS (FIG. 3) supports a two-step mechanism whereby cIAP catalyzes phosphate release from spontaneously hydrolyzed O-PEtN that had initially been bound to LPS in a labile phosphoanhydride linkage.

cIAP Directly Releases Inorganic Phosphate from de-O-acylated Lipid A Chemotypes.

The recalcitrance of all LPS chemotypes thus far tested to being directly dephosphorylated by cIAP suggested that steric interference may prevent the AP active site from engaging target lipid A phosphate monoesters. To test this hypothesis, all ester linked acyl chains from lipid $IV_A$ and Re LPS were removed to generate di-N-acyl de-O-acyl lipid A derivatives (FIG. 5). De-O-acyl lipid A (the N,N-diacylated) only contains amide linked 3-OH—C14:0 acyl chains at C2 of GlcNI and CT of GlcNII. If steric hindrance is indeed problematic, this should facilitate enzyme access to the phosphate groups, particularly at C4' of GlcNII which is now adjacent to a free hydroxyl group in comparison to the steric bulk of a 3-OH—C14:0 acyl chain in lipid $IV_A$. Furthermore, decreasing the acyl chain density on the lipid A backbone substrate also increases the conformational flexibility. Unlike the tetra-acylated lipid $IV_A$ parent, de-O-acyl lipid A was rapidly dephosphorylated in an initial phase that was followed by an extended period of slow phosphate release (FIG. 5A). De-O-acylated Re LPS, which has two Kdo residues attached to C6' of GlcNII (FIG. 12A, inset), was likewise dephosphorylated in a biphasic manner albeit at a slower overall rate (FIG. 5A). MS analysis of cIAP treated products revealed the entire population had lost at least one phosphate group from both de-O-acyl lipid A and Re LPS substrates (FIG. 5B and FIG. 12A). NMR analysis of the residual phosphate remaining after treatment of de-O-acyl lipid A with cIAP indicated the majority (~77%) of the anomeric GlcNI phosphate group was retained under these conditions (FIG. 12B). In sum, the data is consistent with quantitative hydrolysis of a highly cIAP susceptible phosphate group on GlcNII followed by a slower second dephosphorylation event on GlcNI that remains incomplete even after a 48-hour reaction period.

A model of the cIAP active site was generated using the crystal structure of the highly similar rat IAP ortholog as a structural template. Whereas de-O-acyl lipid A could be accommodated within the active site, lipid $IV_A$ could not be docked successfully (FIG. 5C). Detrimental van der Waals contacts arise between the protein surface with the two O-acyl side chains at all times when the GlcNII phosphate was positioned to occupy the active site. In particular, the 3'-O-acyl chain on GlcNII clashed with amino acid chains flanking the active site. During simulations, the N-acylated side chains, however, adopted conformations that could avoid steric clashes when docked with the cIAP susceptible de-O-acyl lipid A GlcNII phosphate orientated in the active site. Likewise, docking of the anomeric C1-GlcNI phosphate lipid $IV_A$ into the catalytic cleft resulted in multiple steric interferences (FIG. 13). The computed binding models are consistent with the non-anomeric 4'-phosphate of de-O-acyl lipid A being the preferred position for cIAP-mediated dephosphorylation PEtN Modification Enhances hTLR4 Agonist Activity of Underacylated LPS Chemotypes.

The data thus far could be coined into a mechanistic model whereby PEtN spontaneously hydrolyzes from phosphoanhydride linkages on LPS to generate free O-PEtN, a monoester substrate that is processed by cIAP to liberate inorganic phosphate. This interpretation would explain the apparent dependence of cIAP for detection of free inorganic phosphate release from LPS under in vitro reaction conditions since the malachite green assay does not detect organic phosphate as in O-PEtN. Yet that alone does not account for the observed decrease in TLR4/MD2 activity after in vitro cIAP treatment considering the critical role lipid A phosphates at C1-GlcNI and C4'-GlcNII play during binding to TLR4/MD2. These data indicate these key phosphate groups remain intact after exposure to cIAP unless primary O-ester acyl chains on lipid A have first been removed. Transforming lipid A into a good cIAP substrate through prior de-O-acylation would itself abrogate TLR4/MD2 activity, which argues against de-O-acyl glycoform dephosphorylation being relevant to endotoxin neutralization.

Previous studies have, however, demonstrated PEtN modifications of lipid A in *Neisseria meningitidis* and *Campylobacter jejuni* increase TLR4/MD2 signaling. Spontaneous hydrolysis of PEtN, which can only be detected by inorganic phosphate assays with added AP, could account for the apparent decrease in biological activity. It was sought to determine whether PEtN modification of *E. coli* lipid A, which has an asymmetric lipid A acyl chain distribution unlike in *N. meningitidis*, impacts TLR4/MD2 recognition in a similar fashion. A strain panel was constructed that synthesized lipid A glycoforms varying in acylation state and either with or without EptA-appended PEtN modifications (FIG. 6A). As expected, comparable amounts of inorganic phosphate were only detected in the presence cIAP with LPS substrates that had been isolated from parent strains expressing EptA (FIG. 6B). TLR4/MD2 stimulation was directly compared using a HEK293/hTLR4/MD2-CD14 whole cell NF-κB reporter assay (FIG. 6C). A luciferase based reporter assay was utilized instead of the secreted embryonic AP (SEAP) Hek-Blue™ colorimetric reporter system, since there are reports that the placental AP (PLAP) isoform dephosphorylates LPS. While PEtN addition to hexa-acylated lipid A had minimal impact, PEtN modifications of the penta- and tetra-acylated lipid A glycoforms containing a full saccharide core enhanced TLR4 signaling by ~10-fold. Tetra-acylated lipid $IV_A$ glycoform did not stimulate hTLR4/MD2, consistent with lipid $IV_A$ being a known human hTLR4 antagonist. PEtN addition by EptA to lipid $IV_A$ imparted low but definite agonist activity (FIG. 6C). Restoration of hTLR4/MD2 activity by PEtN modification of lipid $IV_A$ was suppressed by pre-incubation in buffer in a pH-dependent manner (FIG. 14), as expected considering the labile nature of the lipid $IV_A$-PEtN phosphoanhydride bond with increasing pH (FIGS. 4C and 4D). Collectively this suggests that PEtN addition to lipid $IV_A$ can convert an LPS-like hTLR4 antagonist into a weak agonist. The contribution of PEtN to hTLR4 activity is more determinant with sub-optimal, underacylated *E. coli* LPS ligands, and agrees with observations made using the *N. meningitidis* lipid A scaffold.

Since key amino acid differences at the TLR4/1VD2/LPS interface endow species-specific lipid $IV_A$ responses, the assay was repeated using the same panel of LPS chemotypes but with mouse mTLR4/MD2 expressing NF-κB reporter cells (FIG. 6D). The pattern observed with hTLR4/MD2 was not replicated with the murine receptor complex, as PEtN attachment had minimal effect on signaling for any of the tested lipid A acylation states. This demonstrates that the enhanced signaling observed with hTLR4/MD2 is not an inherent biophysical property of PEtN modified lipid A, but rather due to species-specific ligand recognition and engagement features unique to the respective TLR4/MD2 receptor complexes.

PEtN substitution of Both Lipid $IV_A$ Phosphates is Required for Maximum hTLR4 Agonism.

EptA can covalently add PEtN groups via phosphoanhydride bonds to either of the two lipid A phosphate groups, at C1 of GlcNI or C4' of GlcNII. Hence, it was sought to determine whether both PEtN groups (2-PEtN) are required or if a single PEtN moiety (1-PEtN) is sufficient to trigger hTLR4/MD2 activity. To accomplish this, an *E. coli* B lipid $IV_A$ PEtN producing strain was utilized since this genetic background elaborates higher levels of PEtN modified lipid A in comparison to the K-12 strain used in the prior experiments. A lipid $IV_A$ purification protocol was developed to remove any contaminating lipoproteins and phospholipids, as well as to isolate 1-PEtN and 2-PEtN lipid $IV_A$ species to allow for more quantitative comparisons between glycoforms. Established purification methods used prior for LPS chemotypes containing at least part of the saccharide core failed when applied to PEtN-lipid $IV_A$ material extracted using the PCP method (see Experimental Procedures below). A pair of nonionic detergent aided lipase pre-treatment steps to remove phospholipids and deacylate interfering lipoproteins, which improved the ensuing chromatographic separation of PEtN-lipid $IV_A$ species in the following step (FIG. 15). Using an adapted anion exchange chromatography protocol to separate Ara4N and PEtN modified chemotypes, 2-PEtN and 1-PEtN lipid $IV_A$ species were isolated in high purity. A final purification step using HPLC reverse phase chromatography yielded homogeneous 2- and 1-PEtN lipid $IV_A$ samples that were essentially free of contaminating lipoproteins and chemically pure with respect to PEtN content as judged by MS analysis and TLR2 activation (FIGS. 7A and 7B). In addition, $^{31}P$ NMR analysis confirmed PEtN substitution solely at C4' of GlcNII in the purified 1-PEtN fraction (FIG. 16). When comparing purified fractions, the 2-PEtN fraction alone accounted for the bulk of the recovered hTLR4/MD2 stimulating activity (FIG. 7C). PEtN substitution at C1 of GlcNI on the lipid $IV_A$ scaffold (with four symmetrically distributed acyl chains) therefore constitutes a critical determinant of restoring agonistic character.

Molecular Modeling Suggests hTLR4/MD2 Residues Responsible for Species Specific Enhanced Recognition of PEtN-Modified Lipid A.

Signaling assays with TLR4/MD2 reporter cells unveiled that while lipid $IV_A$ is endotoxically inactive in human receptor complexes as expected, PEtN addition by EptA restores detectable activity (FIGS. 6C and 7C). The contribution of PEtN to enhancing activity was more pronounced as the lipid A ligand became increasingly underacylated (FIG. 6). This trend, however, was not observed in murine receptor (mTLR4/MD2) reporter cells. MD2 is highly conserved between species, except for a few key residues (FIG. 8). In the human receptor complex, a non-conserved cationic residue (hLys122 vs. anionic mGlu122) on the rim of MD2 interacts with the negative charge of lipid A phosphate anions and causes the ligand to be buried more deeply within the MD2 cavity in an antagonistic pose. In contrast, mGlu122 forces the ligand's phosphate groups to move away by charge repulsion into an agonist pose that is well positioned for interactions with other subunits within the complex. Given the constant space in the MD2 binding cleft, underacylated lipid A congeners become more deeply buried than fully acylated ligands in hMD2 until eventually all agonist character is lost as with tetra-acylated lipid $IV_A$. This binding model suggests that as a direct consequence of PEtN substitution, ligand is sufficiently exposed to form contacts with the second TLR4* subunit, triggering dimerization between the [TLR4/MD2] and [TLR4*/MD2*] ectodomains and initiating downstream signaling (FIG. 8). The influence of PEtN groups is thus most evident when needed, i.e. for binding underacylated lipid A ligands in the hTLR4/MD2 complex. This effect is more muted in mTLR4/MD2 since mGlu122 makes the binding contribution of PEtN substitution redundant as mGlu122 already serves a similar function. In addition, there is more potential for favorable electrostatic interaction points between hTLR4 residues (e.g. hAsp294 and hGlu369) with the amino groups of PEtN (FIG. 8B), helping to bridge the space between TLR4 and TLR4*. In contrast, the murine receptor complex with mLys367 in place of hGlu369 is less favorable due to positive charge repulsion.

EXPERIMENTAL PROCEDURES

Reagents

Calf intestinal alkaline phosphatase (cIAP) was purchased from New England BioLabs, human placenta and human liver alkaline phosphatases were from Lee Biosolutions Inc., while porcine kidney alkaline phosphatase was from Sigma. All chemicals were purchased from Sigma Millipore unless noted otherwise.

Bacterial Strain Construction

Gene deletions were introduced into *E. coli* strains using the λ-Red recombinase system as described. Targeting cassettes were obtained by PCR amplification using P1-P2 primer pairs (Table 3). Each primer contained a 5' 42-bp homology extension arm and a 3' 18-bp sequence specific for the indicated antibiotic selection marker of the plasmid template. For the arnA::kanR and lpxM::kanR cassettes, genomic DNA was purified from the Coli Genetic Stock Center strains CGSC #9813 and #9540 and used as a template to flank the antibiotic cassette with FRT sites for subsequent marker excision using the FLP recombinase plasmid pCP20. Integration cassettes were purified and electroporated into recipient strains harboring the arabinose-inducible λ-Red recombinase plasmid pKD46. Plasmids were cured by passaging at 37° C., colonies were checked for loss of plasmid, and cassette insertion was confirmed using check primers (Table 3). For construction of tetra-acylated LPS strains containing a complete saccharide core (GKM499 and GKM502), plasmid pMMW52-msbA was first introduced to enhance LPS transport and improve fitness. In this background, deletion cassettes were then introduced by generalized transduction using P1vir. Strain genotypes are listed in Table 2.

TABLE 2

Bacterial strains and plasmids used in this study.

| Bacterial strain or plasmid | Relevent genotype or phenotype[a] |
|---|---|
| TXM319 | Wild type BL21 (DE3); *E. coli* B F⁻ ompT hsdS_B (r_B⁻ m_B⁻) gal dcm lon λ (DE3 [lacI lacUV5-T7 gene 1 ind1 sam7 nin5]) |
| TXM322 | BL21 (DE3) arnA::kanR; Kan[r] |
| GKM329 | BL21(DE3) eptA::catR; Cat[r] |
| TXM331 | BL21 (DE3) eptA::catR arnA::kanR; Cat[r] Kan[r] |
| TXM333 | BL21 (DE3) lpcA::gentR eptA::catR arnA::kanR; Gent[r] Cat[r] Kan[r] |
| TXM343 | BL21 (DE3) lpcA::gentR eptA::catR arnA::kanR [pSEVA434-eptA]; Gent[r] Cat[r] Kan[r] Spec[r] |
| GKM357 | BL21 (DE3) eptA::catR arnA::kanR waaP::gentR; Cat[r] Kan[r] Gent[r] |
| GKM358 | BL21 (DE3) eptA::catR arnA::kanR waaP::gentR [pSEVA434-eptA]; Cat[r] Kan[r] Gent[r] |
| GKM373 | BL21 (DE3) eptA::catR arnA::kanR eptB::gentR; Cat[r] Kan[r] Gent[r] |
| GKM374 | BL21 (DE3) eptA::catR arnA::kanR eptC::gentR; Cat[r] Kan[r] Gent[r] |
| GKM380 | BL21 (DE3) eptA::catR arnA::kanR eptB::gentR [pSEVA434-eptC]; Cat[r] Kan[r] Gent[r] Spec[r] |
| GKM381 | BL21 (DE3) eptA::catR arnA::kanR eptC::gentR [pSEVA434-eptB]; Cat[r] Kan[r] Gent[r] Spec[r] |
| TXM402 | BL21 (DE3) eptA::catR arnA::kanR eptC::gentR [pSEVA434-eptA]; Cat[r] Kan[r] Gent[r] Spec[r] |
| TXM418 | BL21 (DE3) eptA::catR arnA::FRT eptC::gentR lpxM::kanR; Cat[r] Gent[r] Kan[r] |
| TXM419 | BL21 (DE3) eptA::catR arnA::FRT eptC::gentR lpxM::kanR [pSEVA434-eptA]; Cat[r] Gent[r] Kan[r] Spec[r] |
| GKM445 | ClearColi ® K-12 F⁻, λ⁻ ΔendA ΔrecA msbA52 frr181 ΔgutQΔkdsDΔlpxLΔlpxMΔlpxPΔeptA |
| GKM446 | GKM445 (pSEVA434-eptA); Spec[r] |
| GKM499 | BL21 (DE3) eptA::catR arnA::FRT eptC::gentR lpxM::kanR lpxL::aprR pagP::hygR [pMMW52-msbA]; Cat[r] Gent[r] Kan[r] Apr[r] Hyg[r] Carb[r] |
| GKM502 | BL21 (DE3) eptA::catR arnA::FRT eptC::gentR lpxM::kanR lpxL::aprR pagP::hygR [pMMW52-msbA, pSEVA434-eptA]; Cat[r] Gent[r] Kan[r] Apr[r] Hyg[r] Carb[r] |
| TXM843 | ClearColi ® BL21 (DE3) F⁻ ompT hsdSB (r^B⁻ m^B⁻) gal dcm lon λ (DE3 [lacI lacUV5-T7 |

TABLE 2-continued

Bacterial strains and plasmids used in this study.

| Bacterial strain or plasmid | Relevent genotype or phenotype[a] |
|---|---|
| | gene 1 ind1 sam7 nin5]) msbA148 ΔgutQ ΔkdsD ΔlpxLΔlpxMΔpagPΔlpxP ΔeptA |
| TXM844 | TXM843 [pSEVA434-eptA]; Spec[r] |
| pSEVA434 | pBBR1 ori lacIq-P_trc Spec[r] |
| pSEVA434-eptA | P_trc eptA from *E. coli* BL21 (DE3) |
| pSEVA434-eptB | P_trc eptB from *E. coli* BL21 (DE3) |
| pSEVA434-eptC | P_trc eptC from *E. coli* BL21 (DE3) |
| pMMW52-msbA | pMBL19 carrying a subcloned 3.5-kb insert with ycaI', msbA, and lpxK; Carb[r] |
| pKD3 | Cat[r] template |
| pEXG2 | Gent[r] template |
| pSET152 | Apr[r] template |
| pUC19-oriT-hyg | Hyg[r] template |

[a]Kan[r]—kanamycin; Cat[r]—chloramphenicol; Gent[r]—gentamycin; Spec[r]—spectinomycin; Carb[r]—carbenicillin; Apr[r]—apramycin; Hyg[r]—hygromycin Plasmids expressing either EptA, EptB, or EptC were constructed using the InFusion Cloning kit (Clontech). PCR primer pairs (Table 3) were used to amplify inserts from *E. coli* BL21DE3 genomic DNA and then cloned into the vector pSEVA434 that had been digested with EcoRI/BamHI. Plasmids were maintained with spectinomycin (50 μg/ml) and used without induction as basal expression was sufficient for phenotypic conversion for all three constructs.

TABLE 3

Primers used in this study.

| Primer name | Primer Sequence[a,b] | SEQ ID NO: |
|---|---|---|
| GK425-ArnA::KanR-P1 | GGTGACCTGCCTTACCACAAC | 1 |
| GK426-ArnA::KanR-P2 | TCGTGATGTTTAGCCGCTTC | 2 |
| TM448-EptA::catR-P1 | GTTGGCCGCTTTTTATATCTCTATCTGCCTG AATATTGCCTTGCGCCTACCTGTGACGGA | 3 |
| TM449-EptA::catR-P2 | TGTTGCGTTTGCGCCTGTTTTTGCAGGCAGT TCTGGTCAACCCTTACGCCCCGCCCTGCC | 4 |
| GK429-LpcA::gentR-P1 | CACTGCATTTTGTCTATTACATTTATGCTGA AGGATATCCTCCTCGAATTGACATAAGCCS | 5 |
| GK430-LpcA::gentR-P2 | TGCCGGATGCGGCGTAAACGTCTTATCCGG CCTACGCCAGACGTCGGCTTGAACGAATTG | 6 |
| Tm520-WaaP::gentR-P1 | AGCCGTTTGCCACGTTATGGCGCGGTAAAG ATCCTTTTGAGGCTCGAATTGACATAAGCC | 7 |
| Tm521-WaaP::gentR-P2 | CGTTCTTTCCCTGATTTTTGTGGCTTTTGCT TCTGCTTGCGAGTCGGCTTGAACGAATTG | 8 |
| Tm543-EptB::gentR-P1 | GATACATCAAATCGATTACACAGCAGAAGCT GAGCTTTTTGCCTCGAATTGACATAAGCC | 9 |
| Tm544-EptB::gentR-P2 | GTTAGCCGCTGCCTCTTTTGCCTGCGGGAT GTGACACCAGTTTACGGCTTGAACGAATTG | 10 |
| Tm547-EptC::gentR-P1 | GCATTCCACAGAAGTCCAGGCTAAACCTCTT TTTAGCTGGAACTCGAATTGACATAAGCC | 11 |
| Tm548-EptC::gentR-P2 | CTGATTACCCACCTGATCGCCATACGGCAGT GTGTCGTAATCTACGGCTTGAACGAATTG | 12 |
| Tm582-LpxM::kanR-P1 | GATTTTTGCCTTATCCGAAACTGG | 13 |

TABLE 3 -continued

Primers used in this study.

| Primer name | Primer Sequence$^{a,b}$ | SEQ ID NO: |
|---|---|---|
| Tm583-LpxM::kanR-P2 | CAGGCGAAGGCCTCTCCTCGCGAG | 14 |
| Tm658-LpxL::aprR-P1 | CTACCCAAGTTCTCCACCGCACTGCTTCATC CGCGTTATTGGTCACCTAGATCCTTTTGG | 15 |
| Tm659-LpxL::aprR-P2 | TCCGGGCGTGTTTTAAAGCGACGGTGTAAC CACATATACTGCCGTTCTCCGCTCATGAGC | 16 |
| Tm748-PagP::hygR-P1 | GTTTTATGGTCACAAATGAACGTGAGTAAAT ATGTCGCTATCCTATGACCATGATTACGC | 17 |
| Tm749-PagP::hygR-P2 | ACTAAAACTTCATTTGTCTCAAAACTGAAAG CGCATCCAGGCACGTTGTAAAACGACGGC | 18 |
| GK433-ArnA-check_for | CGAGCGTGAGTTTGGTGAATCC | 19 |
| GK434-ArnA-check_rev | CCGATCCCAGTTACCGCTAC | 20 |
| GK435-EptA-check_for | AAACCCGTATCCCTTAGATGCACC | 21 |
| GK436-EptA-check_rev | CTCAAGGCTTTGTTCCGCCATC | 22 |
| GK431-LpcA-check_for | AGGTCTGACCACTTGTGATG | 23 |
| GK432-LpcA-check_rev | ATTATTCGGCCTACGGTTCG | 24 |
| Tm522-WaaP-check_for | GATAAGCAAATCGCCGATTTCCAG | 25 |
| Tm524-WaaP-check_rev | TGTCTTATTGATCATCTCTTGTGG | 26 |
| Tm545-EptB-checkfor | CAGGGTGTTATCACCTGTTTGTCC | 27 |
| Tm546-EptB-check_rev | CCTTTTGATCGGCGAGAAAGTCAGC | 28 |
| Tm549-EptC-check_for | CCTTAAGGAATTGTCGTTACATTCG | 29 |
| Tm550-EptC-check_rev | GCATCCGGCAAATAGCGCCTGGCTG | 30 |
| Tm614-LpxM-check_for | CTGGCGCAGGCCAAAGAGATTGTGC | 31 |
| Tm615-LpxM-check_rev | GTAGAGTAAGTACGTTGCCGGATGC | 32 |
| Tm660-LpxL-check_for | GGTTGCGGGCGAAAAAATGCGACAATAC | 33 |
| Tm661-LpxL-check_rev | GGGAGATTTAATAGCGTGAAGGAACGC | 34 |
| Tm750-PagP-check_for | GTAGCTTTGCTATGCTAGTAGTAG | 35 |
| Tm751-PagP-check_rev | GTGGTACGCTTTGTCCAGTGTAAC | 36 |
| Tm497-EptA-for_EcoRI | gcggccgcgcgaattAATTTTGCTTTGCGAGC | 37 |
| Tm498-EptA-for_BamHI | cgactctagaggatcCGTCTTCAACAATCAG | 38 |

TABLE 3 -continued

Primers used in this study.

| Primer name | Primer Sequence$^{a,b}$ | SEQ ID NO: |
|---|---|---|
| Tm557-EptB-for_EcoRI | gcggccgcgcgaattCTAAGCAGGGTGTTATC | 39 |
| Tm558-EptB-for_BamHI | cgactctagaggatcCGGCGAGAAAGTCAGCAG | 40 |
| Tm559-EptC-for_EcoRI | gcggccgcgcgaattCTGTCGTTACATTCGGCG | 41 |
| Tm560-EptC-for_BamHI | cgactctagaggatcCGCAAATAGCGCCTGGCTG | 42 |

$^a$Bold case type denotes DNA homology arms used for chromosomal recombination,
$^b$Lower case type indicates homology arms used in plasmid construction.

LPS Purification.

Bacteria were harvested from stationary phase cultures grown at 37° C. in either Lysogeny Broth (10 g tryptone, 5 g yeast extract, 10 g NaCl per liter) or TB media (10 g tryptone, 5 g yeast extract, 3 g NH$_4$Cl, 12 g Na$_2$HPO$_4$, 6 g KH$_2$PO$_4$, 0.5 g Na$_2$SO$_4$, 7.5 g glucose per liter) supplemented with the necessary antibiotics for plasmid selection. Dried bacterial cell biomass was obtained by sequentially stirring in ethanol overnight and then two rounds of acetone (12 hours each) at 4° C., collecting biomass between incubations by centrifugation (6,000×g, 10 min, 4° C.). All LPS and lipid IV$_A$ chemotypes were initially extracted from cell powders via the phenol/chloroform/petroleum ether (PCP) method. Briefly, dried biomass was resuspended in PCP solution (90% phenol/chloroform/petroleum ether in 2:5:8 v/v/v ratio) and incubated for one hour on tube rotator. Biomass was pelleted and the supernatant collected, with the extraction being repeated twice. Pooled supernatant extract was rotavaped to remove chloroform and petroleum ether, and 100 μl of 3 M sodium acetate (pH 7.0) was added to the phenol phase. Here treatment of the samples varied depending on the chemotype. For LPS samples, precipitation was carried out via dropwise addition of water. Pelleted LPS was washed once with 80% phenol and then a second time with acetone. For lipid IV$_A$ samples, five volumes of acetone were added to precipitate lipid IV$_A$ from the phenol phase and then the pellet was washed once with acetone.

To remove co-extracting phospholipids from LPS, samples underwent a modified chloroform/methanol wash. Briefly, pellets were resuspended in chloroform/methanol/3 M sodium acetate (pH 7.0) (85:15:1, v/v/v) and 2 to 3 volumes of methanol were added to precipitate LPS. Phospholipid containing supernatant was decanted and this process was repeated twice. Removal of contaminating lipoprotein was achieved via phenol/sodium deoxycholate extraction as previously described. Lipid IV$_A$ samples could not be efficiently recovered using either the chloroform/methanol wash or the phenol/DOC extraction, hence these steps were omitted.

All chemotypes underwent ultracentrifugation to remove any malachite green reactive nucleic acid material. LPS or lipid IV$_A$ pellets were resuspended in 3 ml of water and added to 30 ml of a Tris-saline buffer (50 mM Tris-HCl, 100 mM NaCl, 1 mM MgCl$_2$, pH 7.0). Samples were centrifuged at 100,000×g for 4-6 hours, resulting in a translucent pellet. The resultant pellet was quickly rinsed with buffer, resuspended in water, and dialyzed (0.5-1 kDa MWCO) against three 5-1 portions of water for 48 hours (24 hours for PEtN-modified chemotypes) at 4° C. Desalted LPS chemotypes were lyophilized to a white powder, while lipid $IV_A$ chemotypes were further purified as described below.

Inorganic Phosphate Release Assay

LPS samples (100 µg/ml) were incubated in alkaline phosphatase buffer [50 mM Tris-HCl at the indicated pH (pH=8.25, 7.4, or 7.1), 100 mM NaCl, 1 mM $MgCl_2$, 20 µM $ZnCl_2$] with either cIAP (4 U/ml), human liver phosphatase (0.1 U/ml), human placenta phosphatase (1 U/ml), or porcine kidney phosphatase (1 U/ml) at 37° C. Aliquots were taken at different time points and phosphate release was measured with the malachite green assay as described previously. Briefly, one volume of malachite green solution (0.1% malachite green, 14% sulfuric acid, 1.5% ammonium molybdate, and 0.18% Tween-20) was mixed with four volumes of LPS solution and the mixture was incubated at room temperature for 10 min. Absorbance was read at 630 nm on SpectraMax Plus 384 plate reader (Molecular Devices). Sodium phosphate was used for standard curve determination. Buffer composition for assays conducted at varying pH values was 50 mM 3-morpholinopropane-1-sulfonic acid (MOPS)-50 mM Tris adjusted to either pH 6.5, 7.4, or 8.5 along with 100 mM NaCl, 1 mM $MgCl_2$ and 20 µM $ZnCl_2$. In the experiments where cIAP was added after pre-incubation in the buffer alone, 10 units of cIAP was added and samples were incubated for 30 min at 37° C. to release inorganic phosphate from spontaneously hydrolyzed PEtN.

TLR4 Stimulation Assay.

HEK293/hTLR4-MD2-CD14, HEK293/mTLR4-MD2-CD14, and parental HEK293/Null2 control cells were grown as specified by the supplier (InvivoGen). For the stimulation assay, the cells were plated at 50,000 cells per well in a white 96 well plate with clear bottom (Costar™ 3610, Corning Incorporated) in 200 µl of growth medium (DMEM, 2 mM 1-glutamine, 10% heat inactivated fetal bovine serum, 50 U/ml penicillin, 50 µg/ml streptomycin, 100 µg/ml Normocin™). The pNiFty-Luc plasmid (InvivoGen) encoding five NF-κB repeated transcription factor binding sites in front of the luciferase reporter gene was mixed with transfection reagent LyoVec™ (InvivoGen) at a concentration of 1 µg of plasmid per 100 µl of LyoVec™, and after incubation at room temperature for 20 min, the mixture (10 µl per well) was added to cells in a 96 well microplate. The next day the medium was removed and replaced with 180 µl of fresh growth medium. Various LPS chemotypes were added at different concentrations in a 20-µl volume per well. Endotoxin-free water was used as a negative control and TNF-α (200 ng/well) was used as a positive control. Pierce™ Firefly Luciferase One-Step Glow Assay Kit was used according to manufacturer's instructions with luminescence being measured after 20 hours of stimulation. All LPS and lipid $IV_A$ preparations were confirmed to be negative for NF-κB induction when challenging HEK293/Null2 control cells (InvivoGen) up to the highest tested LPS concentration (100 ng/ml, data not shown).

TLR2 Stimulation Assay.

HEK-Blue™ hTLR2 cells (InvivoGen) were propagated as specified by the supplier. For the stimulation assay, the cells were plated at 25,000 cells per well in a 96 well plate in 180 µl of growth medium (DMEM, 2 mM 1-glutamine, 10% heat inactivated fetal bovine serum, 50 U/ml penicillin, 50 µg/ml streptomycin, 100 µg/ml Normocin™). LPS was added at different concentrations in a 20 µl per well volume. Endotoxin-free water was used as a negative control.

QUANTI Blue™ (InvivoGen) reagent was used, according to manufacturer's instructions, 20 hours later to detect NF-κB-dependent secreted embryonic alkaline phosphatase (SEAP) activity. Absorbance at 620 nm was read following incubation of the samples with QUANTI Blue™ substrate for 3 hours at 37° C.

Lipase Treatment of Lipid $IV_A$ Extracts.

Crude lipid $IV_A$ (with or without PEtN) was treated with lipase via two sequential incubations. Both 12-hour reactions were conducted at 45° C. in a 20 mM phosphate buffer (pH 7.0). Each reaction contained 40 mg of crude PCP extracted lipid $IV_A$, Thermomyces Lipase (TL, Sigma), and Novozyme® 51032 (Strem Chemicals, Newburyport, MA) at respective final concentrations of 0.1 mg/ml, 90 µg/ml, and 25 µg/ml. The initial reaction included 3.4 mM BIG CHAP (SolTec Bio Science, Beverly, MA) as a nonionic detergent additive. Immediately following this reaction, lipid $IV_A$ was recovered by conversion to a 2:2:1.8 (v/v/v) chloroform/methanol/water Bligh-Dyer biphasic mixture. Lipid $IV_A$ was isolated from the lower organic phase by rotary evaporation, resuspended in endotoxin-free water, and then lyophilized. Recovered lipid $IV_A$ was treated again in a second lipase reaction with 20 mM octyl β-D-glucopyranoside as the detergent additive, and re-isolated as described above. PEtN-modified lipid $IV_A$ was stored at −20° C. until further use.

Chromatographic Purification of Lipid $IV_A$ Species.

Ion exchange chromatography was performed using a 5-ml HiTrap™ SP HP cation exchange column connected in tandem to a 20-ml HiPrep™ DEAE FF 16/10 anion exchange column with the AKTA™ Pure FPLC system. Lipase-treated PEtN lipid $IV_A$ prepared as described above was loaded in 15 ml of a 60% n-propanol solution adjusted to pH 5 with acetic acid. The system was then washed with 10 ml of the same buffer, after which the cation exchange column was removed. The anion exchange column was subsequently washed with 4.5 column volumes of 60% n-propanol (pH 5), before elution using a linear gradient of non-pH adjusted 0 to 80 mM ammonium acetate in 60% n-propanol over 20 column volumes. To identify fractions containing non-volatile organic compounds, 20 µl of each fraction was spotted onto an Analtech Silica gel G TLC plate and visualized by charring using a 10% sulfuric acid-ethanol solution with heating at 160° C. for 10 min. Fractions containing organic material were further analyzed by spotting 20 µl on an Analtec Silica gel H TLC plate, and developed using a pyridine/chloroform/formic acid/water (50:50:16:5, v/v/v/v) mobile phase before sulfuric acid charring. Fractions containing lipid $IV_A$ species were pooled, rotovapped to dryness, and subjected to two rounds of lyophilization to remove residual traces of ammonium acetate. The resulting powder was kept at −20° C. until further purification by reversed-phase high performance liquid chromatography (RP-HPLC). For this, lipid $IV_A$ samples were subjected to RP-HPLC essentially as described, but with some modifications. A semi-preparative Kromasil C18 column (5 µm, 100 Å, 10×250 mm, MZ Analysentechnik, GmbH, Mainz, Germany) was used and samples [resuspended at 5 mg/ml in chloroform/methanol/0.1 M acetic acid (8:2:1, v/v/v)] were eluted using a gradient consisting of methanol/chloroform/water (57:12:31, v/v/v) containing 10 mM ammonium acetate as mobile phase A and chloroform/methanol (70.2:29.8, v/v) with 50 mM ammonium acetate as mobile phase B. The initial solvent system consisted of 2% B and was maintained for 10 min, raised from 2 to 15% B (10-20 min), kept at 15% B for 20 min, raised from 15 to 25% B (40-50 min), kept at 25% B for 20 min, and raised from 25 to 100% B (70-100 min). The solvent was held at 100% B for 20 min, followed by re-equilibration of the column to 2% B for 10 min and held there for an additional 10 min prior to the next injection. The flow rate was 2 ml/min using a splitter between the evaporative light-scattering detector equipped with a low-flow nebulizer (Sedex model 75C ELSD, S.E.D.E.R.E., France). Nitrogen (purity 99.996%) was used as gas to nebulize the post column flow stream at 3.5 bar into the detector at 50° C. setting the photomultiplier gain to 11. The detector signal was transferred to the Gilson HPLC Chemstation (Trilution LC, version 2.1, Gilson) for detection and integration of the ELSD signal.

De-O-acylation and Dephosphorylation of Lipid $IV_A$ and Re LPS with cIAP.

Lipid $IV_A$ was de-O-acylated via base hydrolysis. Lipid A was dissolved (1 to 4 mg/ml) in a 1 M NaOH aqueous solution and incubated for 20 hours at room temperature. Reactions were neutralized via addition of glacial acetic acid while stirring until pH 7.0. Neutralized reactions were extensively dialyzed against water (MWCO: 500-1000 Da) and lyophilized. Re LPS was likewise de-O-acylated, but was recovered by precipitation from neutralized solution using five volumes of ethanol. De-O-acylated products were further purified via anion exchange chromatography as described above. Fractions were pooled, concentrated by rotary evaporation, and dialyzed against water (MWCO: 500-1000 Da). Samples were lyophilized and stored at −20° C.

Large scale (30 ml) cIAP reactions (100 μg/ml de-O-acyl substrate, 4 U/mL cIAP, 50 mM Tris-HCl (pH=7.4), 100 mM NaCl, 1 mM $MgCl_2$, 20 μM $ZnCl_2$) were incubated for 24 to 48-hours at 37° C. Samples were recovered by dialysis against water (100-500 Da MWCO) followed by lyophilization.

Mass Spectrometry

LPS samples were measured on a 7-tesla APEX Qe Electrospray Ionization Fourier Transform Ion Cyclotron Resonance (ESI-FT-ICR) mass spectrometer (Bruker Daltonics). Measurements were performed in negative ion mode. Samples (approximately 0.03 mg/ml) were dissolved in a water/2-propanol/trimethylamine/acetic acid mixture (50:50:0.06:0.02, v/v/v/v). Spectra were acquired in broadband acquisition mode with nano-ESI using the Triversa Nanomate (Advion, Ithaca, NY) as ion source with a spray voltage set to −1.1 kV. Collision voltage was set to 5 V. Lipid $IV_A$ and de-O-acylated samples were measured on a Q Exactive Plus mass spectrometer (Thermo Scientific, Bremen, Germany) using a Triversa Nanomate (Advion, Ithaca, NY) as ion source. For negative ion mode, samples (approximately 0.05 mg/ml) were dissolved in either chloroform/methanol/water (60:35:4.5, v/v/v) or water/propan-2-ol/7M triethylamine/acetic acid mixture (50:50:0.06:0.02, v/v/v/v) and performed with a spray voltage set to −1.1 kV. For positive ion-mode, samples were dissolved in water/propan-2-ol/30 mM ammonium acetate/acetic acid mixture (15:15:1:0.04, v/v/v/v) with a spray voltage set to +1.1 kV. Both mass spectrometers were calibrated externally with glycolipids of known structure. All mass spectra were charge deconvoluted and given mass values refer to the monoisotopic masses of the neutral molecules, if not indicated otherwise.

NMR Spectroscopy.

NMR spectroscopic measurement of PEtN-lipid $IV_A$ was performed in $CDCl_3$/MeOH-$d_4$/$D_2O$ (60:35:8, v/v/v) and de-O-acyl Re LPS after treatment with cIAP in $CDCl_3$/MeOH-$d_4$/$D_2O$ (2:3:1, v/v/v), respectively, at 300 K on a Bruker Avance$^{III}$ 700 MHz (equipped with an inverse 5-mm quadruple-resonance Z-grad cryoprobe). Deuterated solvents were purchased from Deutero GmbH (Kastellaun, Germany). TMS was used as an external standard for calibration of $^1H$ ($\delta_H$ 0.0) and $^{13}C$ ($\delta_C$ 0.0) NMR spectra, and 85% of phosphoric acid was used as an external standard for calibration of $^{31}P$ NMR spectra ($\delta_P$ 0.0). All data were acquired and processed by using Bruker's TOPSPIN V 3.0 software. $^1H$ NMR assignments were confirmed by 2D $^1H$,$^1H$ COSY and total correlation spectroscopy (TOCSY) experiments. $^{13}C$ NMR assignments were indicated by 2D $^1H$,$^{13}C$ HSQC, based on the $^1H$ NMR assignments. Inter-residue connectivity and further evidence for $^{13}C$ assignment were obtained from 2D $^1H$,$^{13}C$ heteronuclear multiple bond correlation and $^1H$,$^{13}C$ HSQC-TOCSY. Connectivity of phosphate groups were assigned by 2D $^1H$ $^{31}P$ HMQC and $^1H$,$^{31}P$ HMQC-TOCSY.

Molecular Modeling.

Standard modeling tools and protocols were conducted according to published protocols. Modeling software [Autodock 4.2, Chimera 1.13.1, SPDBV 4.10, VEGA ZZ 3.1.2] was licensed for academic use to generate and visualize three-dimensional model structures of lipid $IV_A$, TLR4/MD2, and phosphatase enzymes, in addition to partial charges, electrostatic molecular surfaces or fitted active site conformers. The TLR4/MD2 docking protocol was utilized to model LPS-like congener binding. Lipid $IV_A$ and all enzymes and receptors were retrieved from PDB repository server with the exception of hitherto structurally unknown cIAP that was generated by homology modeling using described methodology. The cIAP target (GenBank entry code: AAA30571.1) shares more than 70% identity with rat IAP across 486 non-gapped residues, including all active sites residues. Using the experimentally determined rat IAP crystal structure, a cIAP homodimer structure was generated under Swiss PDB Viewer. Multiple sequence alignments were carried out with built-in Clustal X under Vega ZZ. Of note, all phosphate groups were charged and modeled as monoanionic, e.g. bearing one —OH group. In some figures hydrogen atoms were not displayed for visual simplicity. All model figures were generated with Chimera.

The abbreviations used are:
AP alkaline phosphatase
Ara4N 4-amino-4-deoxy-L-arabinose
cIAP calf intestinal alkaline phosphatase
DAMP damage-associated molecular pattern
EcAP E. coli alkaline phosphatase
Hep L-glycero-D-manno-heptose
IAP intestinal alkaline phosphatase
Kdo 3-deoxy-α-D-manno-oct-2 ulosonic acid
LA lipid A
LBP lipopolysaccharide binding protein
LPS lipopolysaccharide
MAMP microbe-associated molecular pattern
MD2 myeloid differentiation factor-2
ME metabolic endotoxemia
MS mass spectrometry
OM outer membrane
PAMP pathogen-associated molecular pattern
PCP phenol/chloroform/petroleum ether
PEtN phosphoethanolamine
PLAP placental/embryonic alkaline phosphatase
PRR pattern recognition receptors
sCD14 soluble CD14
SEAP secreted embryonic alkaline phosphatase
TLR4 Toll-like receptor 4
TNAP tissue nonspecific alkaline phosphatase Although the present disclosure has been described using specific embodiments and examples, routine modifications will be apparent to those skilled in the art and such modifications are intended to be within the scope of the disclosure and the claims.

The invention claimed is:

1. A PEtN-modified saccharide having the following structure:

Formula XXII where $R^1$ is H;

$R^2$ is independently H or and at least one $R^2$ is $R^3$ is H,

, or

;

71 72
R⁴ is H or
R⁵ is H or
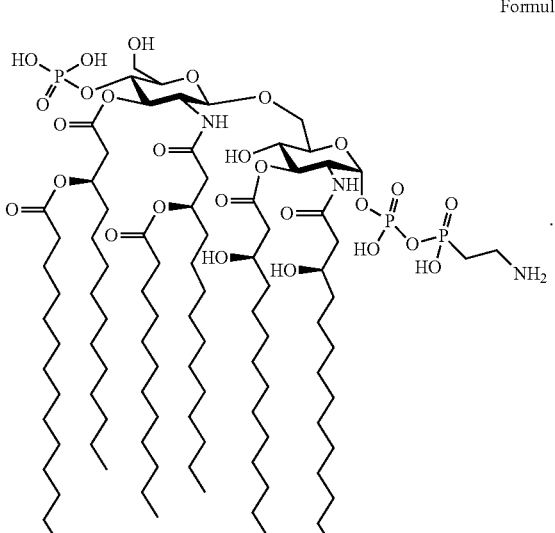
and
2. The PEtN-modified saccharide of claim 1, wherein the PEtN-modified saccharide has the following structure:
Formula XIII
Formula XIV
Formula XV

3. The PEtN-modified saccharide of claim 1, wherein the PEtN-modified saccharide has the following structure:

Formula XVI

Formula XVII                                                          Formula XVIII

4. The PEtN-modified saccharide of claim 1, wherein the PEtN-modified saccharide has the following structure:

Formula XIX

Formula XX

Formula XXI

5. A composition comprising a PEN-modified saccharide of claim 1.

6. The composition of claim 5, further comprising pharmaceutically acceptable carrier.

7. The composition of claim 5, further comprising one or more antigens.

8. The composition of claim 5, further comprising one or more adjuvants.

9. A method for generating or enhancing an immune response in an individual comprising administering to the individual an effective amount of a PEtN-modified saccharide of claim 1 or a composition comprising the PEtN-modified saccharide.

10. The method of claim 9, further comprising administering an antigen against which an immune response is desired.

11. The method of claim 10, wherein the PEtN-modified saccharide and the antigen are administered at the same time.

12. The method of claim 10, wherein the PEtN-modified saccharide and the antigen are administered at different times.

13. The method of claim 10, wherein the antigen is a peptide or protein.

14. The method of claim 10, wherein the PEtN-modified saccharide binds to TLR4.

* * * * *